US011806249B2

(12) United States Patent
Sharifi-Mehr et al.

(10) Patent No.: US 11,806,249 B2
(45) Date of Patent: Nov. 7, 2023

(54) EXPANDABLE INTERBODY IMPLANT WITH LORDOSIS CORRECTION

(71) Applicant: Howmedica Osteonics Corp., Mahwah, NJ (US)

(72) Inventors: Amir Ali Sharifi-Mehr, Bloomingdale, NJ (US); Oliver Buchert, Franklin Lakes, NJ (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 160 days.

(21) Appl. No.: 17/158,499

(22) Filed: Jan. 26, 2021

(65) Prior Publication Data

US 2021/0145600 A1     May 20, 2021

Related U.S. Application Data

(63) Continuation of application No. 15/599,638, filed on May 19, 2017, now Pat. No. 10,940,018.

(Continued)

(51) Int. Cl.
*A61F 2/44*      (2006.01)
*A61F 2/46*      (2006.01)
(Continued)

(52) U.S. Cl.
CPC ............ *A61F 2/447* (2013.01); *A61F 2/4455* (2013.01); *A61F 2/4611* (2013.01); *A61F 2/441* (2013.01);
(Continued)

(58) Field of Classification Search
CPC .. A61F 2/4455–447; A61F 2002/30372; A61F 2002/30471
See application file for complete search history.

(56) References Cited

U.S. PATENT DOCUMENTS 3,875,595 A     4/1975   Froning
4,932,975 A     6/1990   Main et al.
(Continued)

FOREIGN PATENT DOCUMENTS

CN        1756516 A     4/2006
CN    101610741 A     12/2009
(Continued)

OTHER PUBLICATIONS

U.S. Appl. No. 15/481,854, filed Apr. 7, 2017.
(Continued)

*Primary Examiner* — Amy R Sipp
(74) *Attorney, Agent, or Firm* — Duane Morris LLP

(57) ABSTRACT

A spinal implant for placement between vertebral bodies includes a first member for engaging one of the vertebral bodies, a second member for engaging an opposing one of the vertebral bodies, and at least one extendable support element for inducing movement of the entire first member away from the second member. The first member is connected to the second member such that the first member moves away from the second member by a larger distance at a first end of the implant than at a second end of the implant. A connecting member may connect the first and second members together at the second end of the implant. The connecting member may include one or more rotatable linkages, or the connecting member may be an extension of one of the first and second members slidably received within a track defined within the other of the first and second members.

15 Claims, 26 Drawing Sheets

Related U.S. Application Data

(60) Provisional application No. 62/339,459, filed on May 20, 2016.

(51) Int. Cl.
*A61F 2/30* (2006.01)
*A61F 2/48* (2006.01)

(52) U.S. Cl.
CPC ..... *A61F 2/484* (2021.08); *A61F 2002/30329* (2013.01); *A61F 2002/30372* (2013.01); *A61F 2002/30403* (2013.01); *A61F 2002/30471* (2013.01); *A61F 2002/30482* (2013.01); *A61F 2002/30515* (2013.01); *A61F 2002/30537* (2013.01); *A61F 2002/30538* (2013.01); *A61F 2002/4629* (2013.01); *A61F 2002/4692* (2013.01); *A61F 2002/4693* (2013.01)

(56) References Cited

U.S. PATENT DOCUMENTS

| | | | |
|---|---|---|---|
| 4,969,888 A | 11/1990 | Scholten et al. |
| 5,236,460 A | 8/1993 | Barber |
| 5,653,763 A | 8/1997 | Errico et al. |
| 5,665,122 A | 9/1997 | Kambin |
| 5,723,013 A | 3/1998 | Jeanson et al. |
| 5,827,328 A | 10/1998 | Buttermann |
| 5,865,848 A | 2/1999 | Baker |
| 5,916,267 A | 6/1999 | Tienboon |
| 5,980,522 A | 11/1999 | Koros et al. |
| 5,989,290 A | 11/1999 | Biedermann et al. |
| 6,039,761 A | 3/2000 | Li et al. |
| 6,102,950 A | 8/2000 | Vaccaro |
| 6,127,597 A | 10/2000 | Beyar et al. |
| 6,159,244 A | 12/2000 | Suddaby |
| 6,176,881 B1 | 1/2001 | Schar et al. |
| 6,193,756 B1 | 2/2001 | Studer et al. |
| 6,214,012 B1 | 4/2001 | Karpman et al. |
| 6,296,665 B1 | 10/2001 | Strnad et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,032 B1 | 5/2002 | Gauchet |
| 6,454,806 B1 | 9/2002 | Cohen et al. |
| 6,527,803 B1 | 3/2003 | Crozet et al. |
| 6,562,074 B2 | 5/2003 | Gerbec et al. |
| 6,582,467 B1 | 6/2003 | Teitelbaum et al. |
| 6,585,699 B2 | 7/2003 | Ljunggreen et al. |
| 6,692,495 B1 | 2/2004 | Zacouto |
| 6,719,796 B2 | 4/2004 | Cohen et al. |
| 6,723,126 B1 | 4/2004 | Berry |
| 6,730,088 B2 | 5/2004 | Yeh |
| 6,764,491 B2 | 7/2004 | Frey et al. |
| 6,830,570 B1 | 12/2004 | Frey et al. |
| 6,835,207 B2 | 12/2004 | Zacouto et al. |
| 6,866,682 B1 | 3/2005 | An et al. |
| 6,875,235 B2 | 4/2005 | Ferree |
| 6,953,477 B2 | 10/2005 | Berry |
| 6,960,232 B2 | 11/2005 | Lyons et al. |
| 6,981,989 B1 | 1/2006 | Fleischmann et al. |
| 7,001,431 B2 | 2/2006 | Bao et al. |
| 7,018,415 B1 | 3/2006 | McKay |
| 7,018,416 B2 | 3/2006 | Hanson et al. |
| 7,060,037 B2 | 6/2006 | Lussier et al. |
| 7,060,073 B2 | 6/2006 | Frey et al. |
| 7,066,958 B2 | 6/2006 | Ferree |
| 7,094,257 B2 | 8/2006 | Mujwid et al. |
| 7,166,110 B2 | 1/2007 | Yundt |
| 7,204,853 B2 | 4/2007 | Gordon et al. |
| 7,214,243 B2 | 5/2007 | Taylor |
| 7,217,293 B2 | 5/2007 | Branch, Jr. |
| 7,282,063 B2 | 10/2007 | Cohen et al. |
| 7,291,150 B2 | 11/2007 | Graf |
| 7,291,158 B2 | 11/2007 | Crow et al. |
| 7,316,686 B2 | 1/2008 | Dorchak et al. |
| 7,316,714 B2 | 1/2008 | Gordon et al. |
| 7,351,261 B2 | 4/2008 | Casey |
| 7,407,513 B2 | 8/2008 | Alleyne et al. |
| 7,419,505 B2 | 9/2008 | Fleischmann et al. |
| 7,452,359 B1 | 11/2008 | Michelson |
| 7,470,273 B2 | 12/2008 | Dougherty-Shah |
| 7,481,812 B2 | 1/2009 | Frey et al. |
| 7,485,145 B2 | 2/2009 | Purcell |
| 7,507,241 B2 | 3/2009 | Levy et al. |
| 7,520,900 B2 | 4/2009 | Trieu |
| 7,537,664 B2 | 5/2009 | O'Neill et al. |
| 7,563,284 B2 | 7/2009 | Coppes et al. |
| 7,563,286 B2 | 7/2009 | Gerber et al. |
| 7,621,956 B2 | 11/2009 | Paul et al. |
| 7,628,815 B2 | 12/2009 | Baumgartner et al. |
| 7,670,359 B2 | 3/2010 | Yundt |
| 7,708,779 B2 | 5/2010 | Edie et al. |
| 7,722,674 B1 | 5/2010 | Grotz |
| 7,731,752 B2 | 6/2010 | Edie et al. |
| 7,731,753 B2 | 6/2010 | Reo et al. |
| 7,771,480 B2 | 8/2010 | Navarro et al. |
| 7,794,501 B2 | 9/2010 | Edie et al. |
| 7,806,935 B2 | 10/2010 | Navarro et al. |
| 7,819,921 B2 | 10/2010 | Grotz |
| 7,824,444 B2 | 11/2010 | Biscup et al. |
| 7,824,445 B2 | 11/2010 | Biro et al. |
| 7,854,766 B2 | 12/2010 | Moskowitz et al. |
| 7,862,618 B2 | 1/2011 | White et al. |
| 7,883,543 B2 | 2/2011 | Sweeney |
| 7,935,124 B2 | 5/2011 | Frey et al. |
| 7,967,863 B2 | 6/2011 | Frey et al. |
| 7,967,867 B2 | 6/2011 | Barreiro et al. |
| 7,985,231 B2 | 7/2011 | Sankaran |
| 7,985,256 B2 | 7/2011 | Grotz et al. |
| 8,021,395 B2 | 9/2011 | Ben-Mokhtar et al. |
| 8,025,680 B2 | 9/2011 | Hayes et al. |
| 8,057,549 B2 | 11/2011 | Butterman et al. |
| 8,062,368 B2 | 11/2011 | Heinz et al. |
| 8,062,373 B2 | 11/2011 | Fabian, Jr. |
| 8,070,813 B2 | 12/2011 | Grotz et al. |
| 8,105,382 B2 | 1/2012 | Olmos et al. |
| 8,147,861 B2 | 4/2012 | Jones et al. |
| 8,153,785 B2 | 4/2012 | Khire et al. |
| 8,187,331 B2 | 5/2012 | Strohkirch, Jr. et al. |
| 8,192,495 B2 | 6/2012 | Simpson et al. |
| 8,267,939 B2 | 9/2012 | Cipoletti et al. |
| 8,273,124 B2 | 9/2012 | Renganath et al. |
| 8,303,663 B2 | 11/2012 | Jimenez et al. |
| 8,350,186 B2 | 1/2013 | Jones et al. |
| 8,353,961 B2 | 1/2013 | McClintock et al. |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,480,741 B2 | 7/2013 | Grotz et al. |
| 8,696,751 B2 | 4/2014 | Ashley et al. |
| 8,728,387 B2 | 5/2014 | Jones et al. |
| 8,992,620 B2 | 3/2015 | Ashley et al. |
| 8,992,703 B2 | 3/2015 | O'Neill et al. |
| 8,998,924 B2 | 4/2015 | Simpson et al. |
| 9,028,550 B2 | 5/2015 | Shulock et al. |
| 9,135,374 B2 | 9/2015 | Jones et al. |
| 9,180,010 B2 | 11/2015 | Dong et al. |
| 9,662,224 B2 | 5/2017 | Weiman et al. |
| 2001/0056302 A1 | 12/2001 | Boyer et al. |
| 2002/0128716 A1 | 9/2002 | Cohen et al. |
| 2002/0136146 A1 | 9/2002 | Lee et al. |
| 2002/0138146 A1 | 9/2002 | Jackson |
| 2002/0151976 A1 | 10/2002 | Foley et al. |
| 2003/0114899 A1 | 6/2003 | Woods et al. |
| 2003/0130739 A1 | 7/2003 | Gerbec et al. |
| 2004/0030346 A1 | 2/2004 | Frey et al. |
| 2004/0088054 A1 | 5/2004 | Berry |
| 2004/0097928 A1 | 5/2004 | Zdeblick et al. |
| 2004/0133273 A1 | 7/2004 | Cox |
| 2004/0153065 A1 | 8/2004 | Lim |
| 2004/0153156 A1 | 8/2004 | Cohen et al. |
| 2004/0181229 A1 | 9/2004 | Michelson |
| 2004/0186576 A1 | 9/2004 | Biscup et al. |

(56) References Cited

U.S. PATENT DOCUMENTS

| | | |
|---|---|---|
| 2005/0033437 A1 | 2/2005 | Bao et al. |
| 2005/0043800 A1 | 2/2005 | Paul et al. |
| 2005/0049590 A1 | 3/2005 | Alleyne et al. |
| 2005/0085910 A1 | 4/2005 | Sweeney |
| 2005/0107881 A1 | 5/2005 | Alleyne et al. |
| 2005/0113842 A1 | 5/2005 | Bertagnoli et al. |
| 2005/0197702 A1 | 9/2005 | Coppes et al. |
| 2005/0216084 A1 | 9/2005 | Fleischmann et al. |
| 2005/0229433 A1 | 10/2005 | Cachia |
| 2005/0251260 A1 | 11/2005 | Gerber et al. |
| 2005/0273169 A1 | 12/2005 | Purcell |
| 2005/0273170 A1 | 12/2005 | Navarro et al. |
| 2005/0273171 A1 | 12/2005 | Gordon et al. |
| 2006/0036259 A1 | 2/2006 | Carl et al. |
| 2006/0085073 A1 | 4/2006 | Raiszadeh |
| 2006/0089719 A1 | 4/2006 | Trieu |
| 2006/0106416 A1 | 5/2006 | Raymond et al. |
| 2006/0116767 A1 | 6/2006 | Magerl et al. |
| 2006/0142860 A1 | 6/2006 | Navarro et al. |
| 2006/0142861 A1 | 6/2006 | Murray |
| 2006/0147332 A1 | 7/2006 | Jones et al. |
| 2006/0149377 A1 | 7/2006 | Navarro et al. |
| 2006/0167547 A1 | 7/2006 | Suddaby |
| 2006/0200244 A1 | 9/2006 | Assaker |
| 2006/0235426 A1 | 10/2006 | Lim et al. |
| 2006/0235535 A1 | 10/2006 | Ferree et al. |
| 2006/0264968 A1 | 11/2006 | Frey et al. |
| 2007/0050030 A1 | 3/2007 | Kim |
| 2007/0050033 A1 | 3/2007 | Reo et al. |
| 2007/0073395 A1 | 3/2007 | Baumgartner et al. |
| 2007/0093901 A1 | 4/2007 | Grotz et al. |
| 2007/0093903 A1 | 4/2007 | Cheng |
| 2007/0123987 A1 | 5/2007 | Bernstein |
| 2007/0179611 A1 | 8/2007 | DiPoto et al. |
| 2007/0233254 A1 | 10/2007 | Grotz et al. |
| 2007/0255409 A1 | 11/2007 | Dickson et al. |
| 2007/0255413 A1 | 11/2007 | Edie et al. |
| 2007/0255415 A1 | 11/2007 | Edie et al. |
| 2007/0270961 A1 | 11/2007 | Ferguson |
| 2007/0270964 A1 | 11/2007 | Strohkirch et al. |
| 2007/0288092 A1 | 12/2007 | Bambakidis |
| 2008/0021555 A1 | 1/2008 | White et al. |
| 2008/0021556 A1 | 1/2008 | Edie |
| 2008/0058930 A1 | 3/2008 | Edie et al. |
| 2008/0058931 A1 | 3/2008 | White et al. |
| 2008/0065082 A1 | 3/2008 | Chang et al. |
| 2008/0065220 A1 | 3/2008 | Alleyne et al. |
| 2008/0065221 A1 | 3/2008 | Alleyne et al. |
| 2008/0077150 A1 | 3/2008 | Nguyen |
| 2008/0086276 A1 | 4/2008 | Naka et al. |
| 2008/0097441 A1 | 4/2008 | Hayes et al. |
| 2008/0103601 A1 | 5/2008 | Biro et al. |
| 2008/0114467 A1 | 5/2008 | Capote et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0161933 A1 | 7/2008 | Grotz et al. |
| 2008/0177387 A1 | 7/2008 | Parimore et al. |
| 2008/0215153 A1 | 9/2008 | Butterman et al. |
| 2008/0281424 A1 | 11/2008 | Parry et al. |
| 2008/0288073 A1 | 11/2008 | Renganath et al. |
| 2008/0300598 A1 | 12/2008 | Barreiro et al. |
| 2009/0005819 A1 | 1/2009 | Ben-Mokhtar et al. |
| 2009/0005874 A1 | 1/2009 | Fleischmann et al. |
| 2009/0018661 A1 | 1/2009 | Kim et al. |
| 2009/0043312 A1 | 2/2009 | Koulisis et al. |
| 2009/0048676 A1 | 2/2009 | Fabian, Jr. |
| 2009/0105836 A1 | 4/2009 | Frey et al. |
| 2009/0171389 A1 | 7/2009 | Sankaran |
| 2009/0204215 A1 | 8/2009 | McClintock et al. |
| 2009/0216331 A1 | 8/2009 | Grotz et al. |
| 2009/0222100 A1 | 9/2009 | Cipoletti et al. |
| 2009/0270987 A1 | 10/2009 | Heinz et al. |
| 2010/0016970 A1 | 1/2010 | Kapitan et al. |
| 2010/0057204 A1 | 3/2010 | Kadaba et al. |
| 2010/0145455 A1 | 6/2010 | Simpson et al. |
| 2010/0145456 A1 | 6/2010 | Simpson et al. |
| 2010/0249930 A1 | 9/2010 | Myers |
| 2011/0130835 A1 | 6/2011 | Ashley et al. |
| 2011/0137416 A1 | 6/2011 | Myers |
| 2011/0138948 A1 | 6/2011 | Jimenez et al. |
| 2011/0270398 A1 | 11/2011 | Grotz et al. |
| 2011/0288646 A1 | 11/2011 | Moskowitz et al. |
| 2012/0059469 A1 | 3/2012 | Myers et al. |
| 2012/0116518 A1 | 5/2012 | Grotz et al. |
| 2012/0130387 A1 | 5/2012 | Simpson et al. |
| 2012/0245695 A1 | 9/2012 | Simpson et al. |
| 2012/0283830 A1 | 11/2012 | Myers |
| 2013/0096677 A1 | 4/2013 | Myers et al. |
| 2013/0158664 A1 | 6/2013 | Palmatier et al. |
| 2013/0158669 A1 | 6/2013 | Sungarian et al. |
| 2013/0197642 A1 | 8/2013 | Ernst |
| 2013/0197647 A1 | 8/2013 | Wolters et al. |
| 2013/0197648 A1 | 8/2013 | Boehm et al. |
| 2013/0204368 A1 | 8/2013 | Prevost |
| 2013/0204374 A1 | 8/2013 | Milella, Jr. |
| 2013/0253650 A1 | 9/2013 | Ashley et al. |
| 2014/0316522 A1* | 10/2014 | Weiman ............... A61F 2/4611 623/17.16 |
| 2015/0025634 A1* | 1/2015 | Boehm ............... A61F 2/4465 623/17.15 |
| 2015/0112352 A1 | 4/2015 | Krause et al. |
| 2015/0351925 A1 | 12/2015 | Emerick et al. |
| 2016/0022434 A1 | 1/2016 | Robinson |
| 2016/0089247 A1 | 3/2016 | Nichols et al. |
| 2016/0199193 A1 | 7/2016 | Willis et al. |
| 2017/0296352 A1 | 10/2017 | Richerme et al. |
| 2017/0312090 A1 | 11/2017 | Sharabani et al. |

FOREIGN PATENT DOCUMENTS

| | | |
|---|---|---|
| CN | 101631516 A | 1/2010 |
| CN | 101686860 A | 3/2010 |
| CN | 101686865 B | 5/2013 |
| EP | 1442715 A3 | 11/2004 |
| EP | 1415624 B1 | 5/2006 |
| FR | 3026294 A1 | 4/2016 |
| JP | 2001-518824 A | 10/2001 |
| JP | 2008-502372 A | 1/2008 |
| WO | 2003003951 A1 | 1/2003 |
| WO | 2004016250 A1 | 2/2004 |
| WO | 2004016205 A3 | 5/2004 |
| WO | 2006044786 A3 | 1/2007 |
| WO | 2008011371 A3 | 3/2008 |
| WO | 2007124078 A3 | 7/2008 |
| WO | 2008039811 A3 | 7/2008 |
| WO | 2008112607 A3 | 12/2008 |
| WO | 2008148210 A1 | 12/2008 |
| WO | 2009033100 A1 | 3/2009 |
| WO | 2008121251 A3 | 8/2009 |
| WO | 2009064787 A3 | 8/2009 |
| WO | 2009105182 A1 | 8/2009 |
| WO | 2009114381 A1 | 9/2009 |
| WO | 2008086276 A3 | 12/2009 |
| WO | 2010074704 A1 | 7/2010 |
| WO | 2010068725 A3 | 10/2010 |
| WO | 2011011609 A3 | 6/2011 |
| WO | 2011150077 A1 | 12/2011 |
| WO | 2013173767 A1 | 11/2013 |
| WO | 2014144696 A1 | 9/2014 |
| WO | 0156513 A1 | 1/2015 |
| WO | 2015198335 A1 | 12/2015 |
| WO | 2016063283 A1 | 4/2016 |
| WO | 2016183382 A1 | 11/2016 |
| WO | 2017117513 A1 | 7/2017 |

OTHER PUBLICATIONS

U.S. Appl. No. 15/480,781, filed Apr. 6, 2017.
U.S. Appl. No. 15/241,339, filed Aug. 19, 2016.
U.S. Appl. No. 62/319,460, filed Aug. 7, 2016.
U.S. Appl. No. 62/245,004, filed Oct. 22, 2015.

(56) References Cited

OTHER PUBLICATIONS

Extended European Search Report for Application No. 17172001.4 dated Sep. 28, 2017.
Official Action for European Patent Application No. 17172004.1 dated Oct. 4, 2022, 6 pages.

* cited by examiner

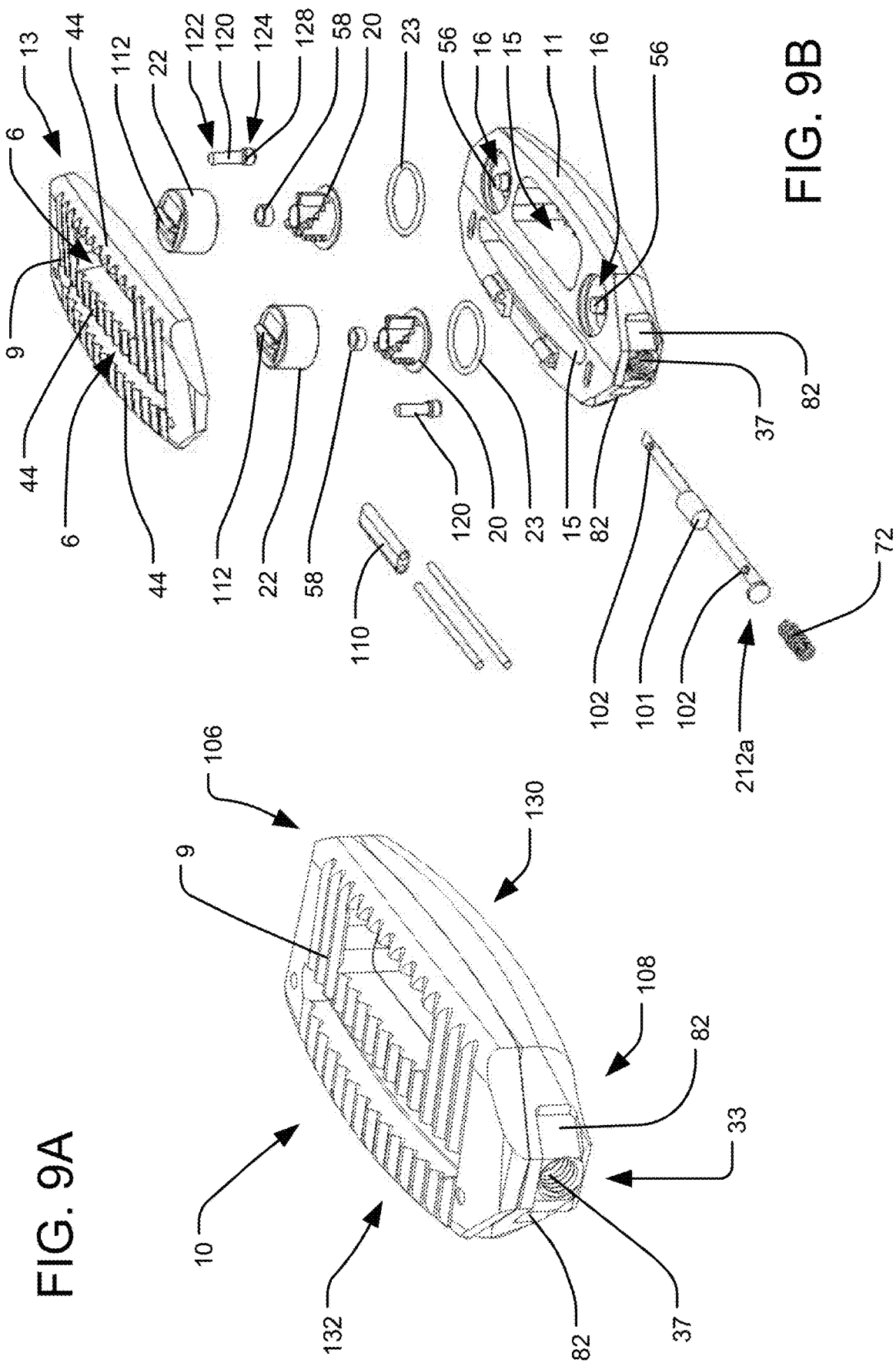

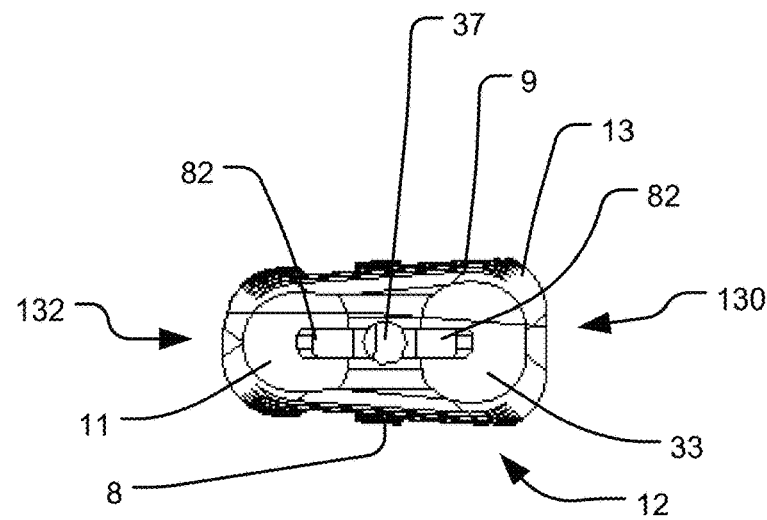

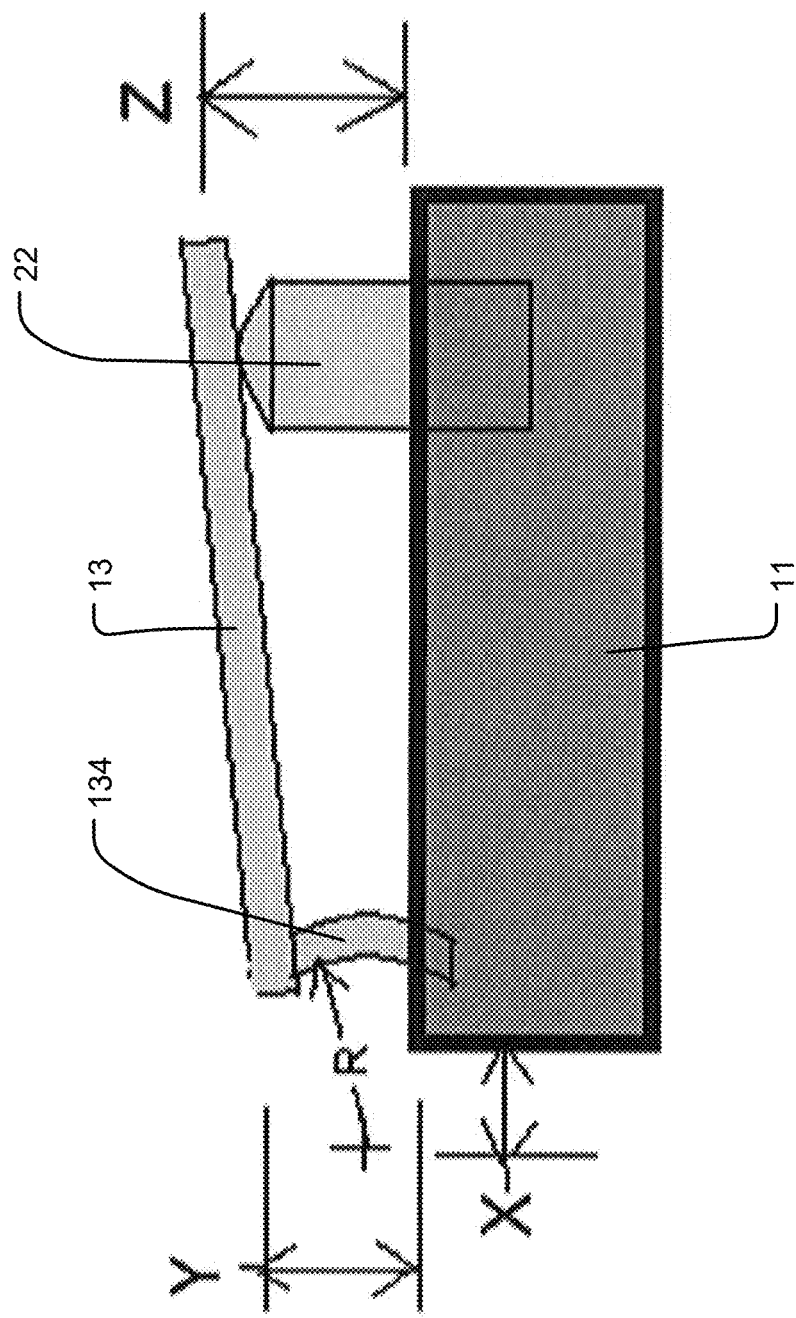

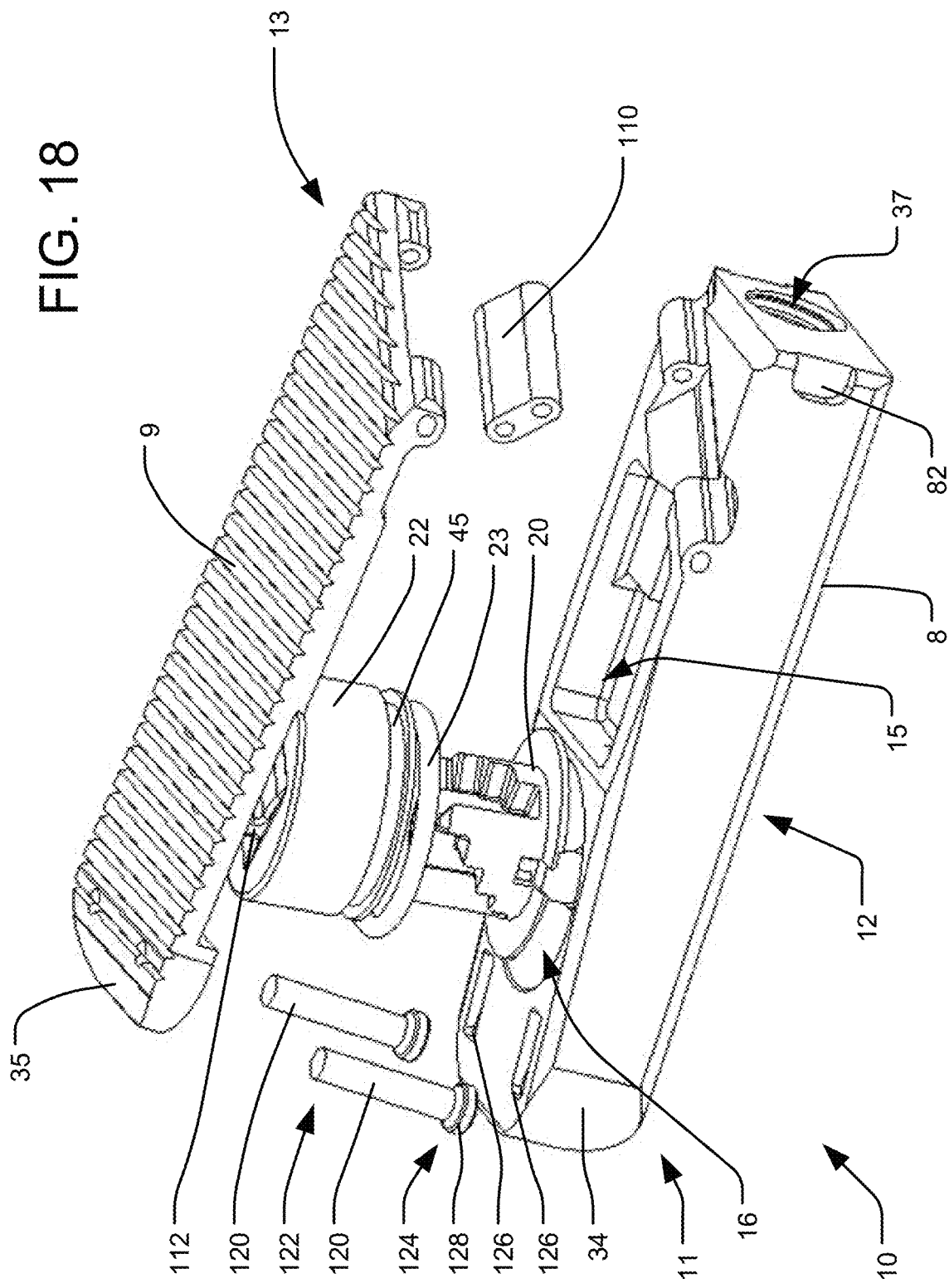

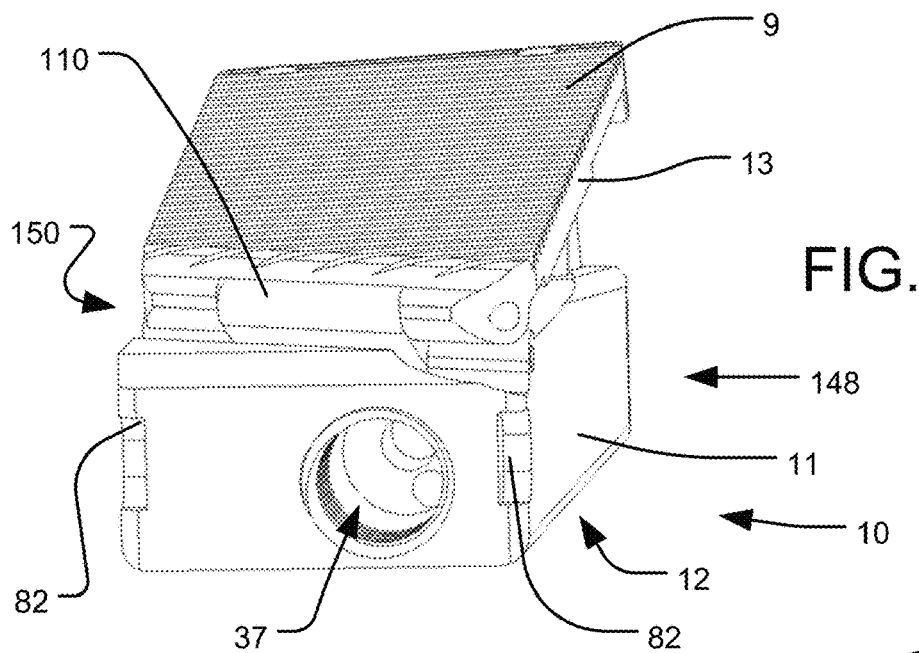
FIG. 19C
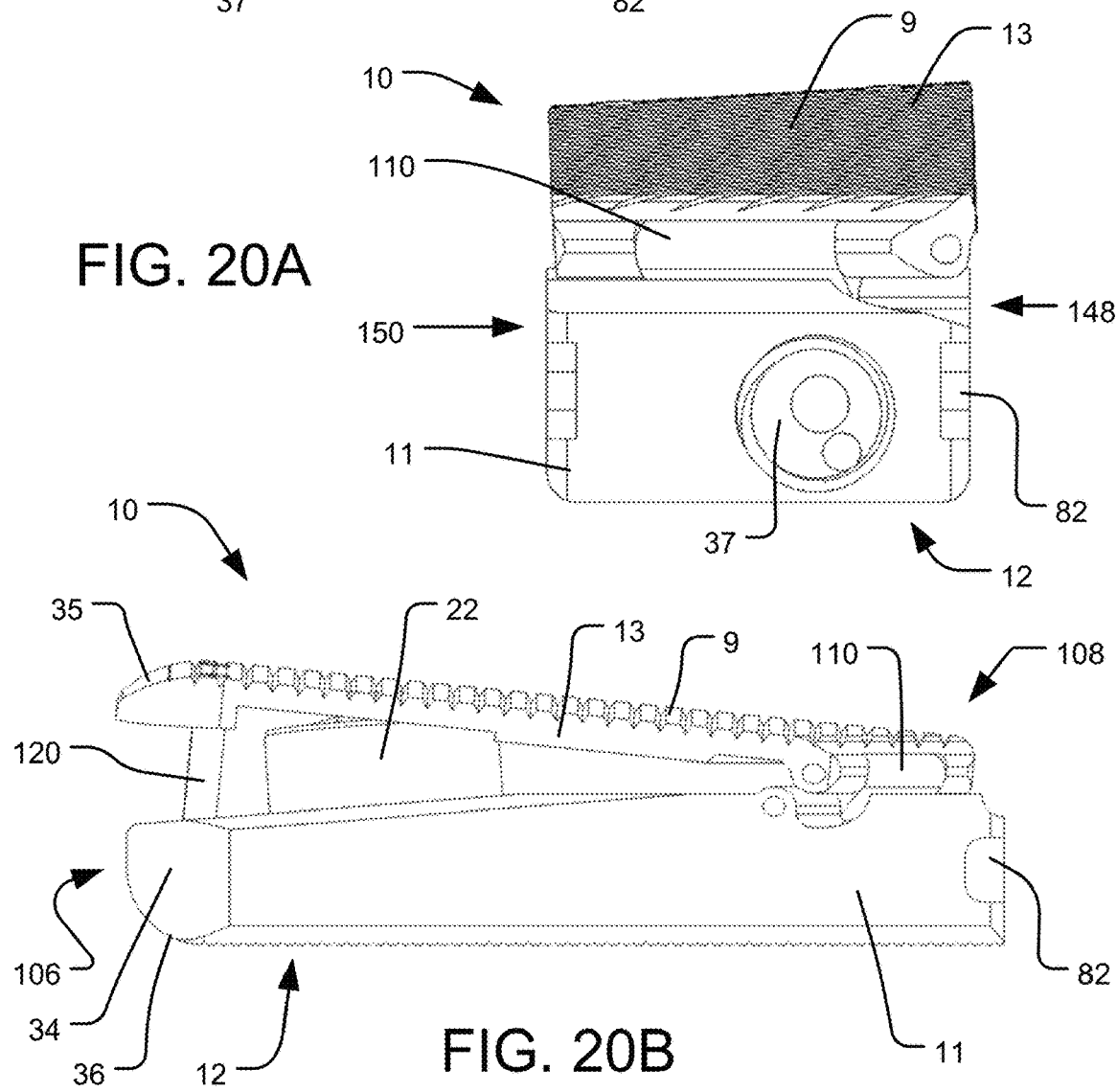
FIG. 20A
FIG. 20B

EXPANDABLE INTERBODY IMPLANT WITH LORDOSIS CORRECTION

CROSS-REFERENCE TO RELATED APPLICATIONS

This application is a continuation of U.S. patent application Ser. No. 15/599,638 filed May 19, 2017, which claims the benefit of the filing date of U.S. Provisional Patent Application No. 62/339,459 filed May 20, 2016, the disclosures of which are hereby incorporated herein by reference.

BACKGROUND OF THE INVENTION

Intervertebral implants are commonly used in spinal surgery, such as in interbody fusion procedures, in which an implant (e.g., a spacer or cage) is placed in the disc space between two vertebrae to be fused together. At least a portion of the disc is typically removed before the implant is positioned in the intervertebral space, and the implant may be supplemented with bone graft material to promote fusion of the vertebrae. Interbody fusion procedures may also be performed in conjunction with other types of fixation, such as pedicle screw fixation, to provide additional stability, particularly while the vertebrae fuse together.

Different interbody fusion procedures can be distinguished by their location along the spine (e.g., in the cervical, thoracic, or lumbar regions); by the type of implant used; and by the surgical approach to the intervertebral space, in which different surgical approaches often imply different structural characteristics of the implant or implants used. Different surgical approaches to the spine include anterior, posterior, and lateral. Examples of interbody fusion techniques performed along a posterior approach include posterior lumbar interbody fusion (PLIF) and transforaminal lumbar interbody fusion (TLIF). PLIF techniques typically include positioning two intervertebral implants into the intervertebral space along a posterior to anterior direction, with one implant being positioned towards the left side of the spine and one implant being positioned towards the right side of the spine. The implants used in such PLIF techniques typically have a straight shape, in that they extend along a central axis. TLIF techniques, by contrast, typically include positioning one intervertebral implant into the intervertebral space (often towards the anterior portion of the intervertebral space) from the posterior of the patient, but the spine is approached on one side from a more lateral position than in PLIF techniques. The implants used in such TLIF techniques are often curved, such that they have an overall kidney bean-like shape. Interbody fusion techniques performed along a lateral approach, on the other hand, often involve implants that are generally symmetric along their linear longitudinal axis (e.g., having a substantially rectangular or oval shape), but the implants are typically larger than those used in PLIF or TLIF techniques. That is, intervertebral implants used in lateral approaches often cover a substantial portion of the disc space.

Included among the different types of intervertebral implants are expandable implants. Such implants often have an initially contracted configuration, such that they have a low profile in the superior-inferior direction, in order to ease insertion into the intervertebral space. Such expandable implants can then be expanded in the superior-inferior direction after implantation, so as to securely engage and stabilize the vertebrae on both sides of the intervertebral space. Examples of such expandable intervertebral implants are disclosed in U.S. Pat. No. 8,992,620 ("the '620 Patent") and in U.S. patent application Ser. No. 15/481,854 filed on Apr. 7, 2017, entitled Expandable Interbody Implant (hereinafter "the '854 Application"), the disclosures of which are hereby incorporated by reference herein as if fully set forth herein. Expandable intervertebral implants having certain similar features to those in the '620 Patent and the '854 Application are disclosed herein, and therefore some similar nomenclature is used herein for clarity and consistency.

Although considerable effort has been devoted in the art to optimization of such intervertebral systems and methods, still further improvement would be desirable.

BRIEF SUMMARY OF THE INVENTION

The present invention relates to expandable interbody implants, as well as to methods of operating the same. Expandable interbody implants in accordance with aspects of the invention include opposing first and second surfaces for engaging respective vertebral bodies on each side of an intervertebral space, the first and second surfaces being located on respective first and second members. When the implants are expanded from a contracted configuration to an expanded configuration, the entire first member is moved away from the second member. The first member is desirably connected to the second member such that the first member moves away from the second member by a larger distance at a first end of the implant than at a second end of the implant. At least one extendable support element may be connected between the first and second members, which extendable support element may be actuatable to induce the movement of the entire first member away from the second member. The first member may be connected to the second member by a connecting member positioned at the second end of the implant. The extendable support element may drive the movement of the first member away from the second member at both the first and second ends of the implant. The entire movement of the first member may be induced by a single source, such as one or more extendable support elements controlled by the same source. The connecting member may constrain the movement of the first member at the second end to follow a defined path, based on that movement of the first member induced by the single source.

A spinal implant for placement between first and second vertebral bodies, in accordance with an aspect of the invention, includes first and second members having respective first and second surfaces for engaging respective vertebral bodies. The first and second surfaces may be on opposing sides of the implant to engage the respective vertebral bodies on each side of the intervertebral space. The implant may include at least one extendable support element connected between the first and second members. The extendable support element is desirably actuatable to induce movement of the entire first member away from the second member. The first and second members are preferably connected together such that, when movement of the first member away from the second member is induced by the extendable support element, the first member moves away from the second member by a larger distance at a first end of the implant than at a second end of the implant.

In accordance with other aspects of the invention, the first member may be connected to the second member by a connecting member positioned at the second end of the implant. In accordance with some such aspects of the invention, the connecting member may extend at an oblique angle to the longitudinal axis of the implant, the longitudinal axis extending between the first and second ends of the implant. In accordance with other such aspects of the invention, the connecting member may be a rotatable linkage. A first end of the linkage may be pivotably connected to the first member and a second end of the linkage may be pivotably connected to the second member. In accordance with yet other such aspects of the invention, the connecting member may include a plurality of rotatable linkages connected between the first and second members. In accordance with yet other such aspects of the invention, the connecting member may be an extension of the first member which is slidably received within a track defined within the second member. In accordance with other aspects of the invention, the connecting member may be configured such that the first member rotates about a point spaced apart from the implant proximate the second end of the implant. For example, the extension and the track may be curved so as to constrain the movement of the first member away from the second member such that the first member rotates about a point spaced apart from the implant proximate the second end of the implant.

In accordance with other aspects of the invention, the extendable support element may be positioned intermediate the first and second ends of the implant. In accordance with some such aspects of the invention, the extendable support element may be rigidly mounted to the second member at an oblique angle with respect to the second surface. In accordance with other such aspects of the invention, the extendable support element may be configured to be extended by a fluid. In accordance with yet other such aspects of the invention, the extendable support element may be rigidly mounted to the second member, and the extendable support element may be connected to the first member by a pivotable connection such that the first member can pivot with respect to the extendable support element. In accordance with yet other such aspects of the invention, the extendable support element may be rigidly mounted to the second member, and the extendable support element may slidably engage the first member. For example, the extendable support element may slidably engage the first member along mating curved surfaces.

In accordance with other aspects of the invention, the implant may include at least one post extending between the first and second members, which post constrains the maximum movement of the first member away from the second member. In accordance with some such aspects of the invention, the post may be positioned proximate the first end of the implant, such that the post constrains the maximum movement of the first member away from the second member at the first end.

In accordance with other aspects of the invention, the first end of the implant may be at a distal end of the implant and the second end of the implant may be at a proximal end of the implant, where the implant has a longitudinal axis extending between the distal and proximal ends. In accordance with some such aspects of the invention, the implant may include a connector at the second end of the implant that is structured to securely engage an inserter for positioning the implant.

In accordance with other aspects of the invention, the implant may extend along a longitudinal axis between distal and proximal ends of the implant, where the first end of the implant is positioned on one side of the longitudinal axis and the second end of the implant is positioned on an opposing side of the longitudinal axis from the first end. In accordance with some such aspects of the invention, the implant may include a connector at the proximal end of the implant that is structured to securely engage an inserter for positioning the implant. In accordance with other such aspects of the invention, the at least one extendable support element includes first and second extendable support elements spaced apart along the longitudinal axis of the implant. In accordance with yet other such aspects of the invention, the longitudinal axis may be curved, such that the implant has a curved, kidney bean-like shape between its proximal and distal ends.

BRIEF DESCRIPTION OF THE DRAWINGS

FIG. 9A is a perspective view of an implant in accordance with another embodiment of the present invention in a contracted configuration.

FIG. 9B is an exploded, perspective view of the embodiment of the implant of FIG. 9A.

FIG. 10A is a top plan view of the embodiment of the implant of FIG. 9A.

FIG. 10B is a front elevation view of the embodiment of the implant of FIG. 9A in a contracted configuration.

FIG. 10C is a rear elevation view of the embodiment of the implant of FIG. 9A in a contracted configuration.

FIG. 13 is a schematic illustration of certain geometrical relationships in connection with implants in accordance with embodiments of the present invention.

FIG. 18 is an exploded, perspective view of the embodiment of the implant of FIGS. 17A-B.

FIG. 19C is a rear perspective view of the embodiment of the implant of FIGS. 17A-B in an extended configuration.

FIG. 20A is a rear elevation view of the embodiment of FIGS. 17A-B in an extended configuration.

FIG. 20B is a side elevation view of the embodiment of FIGS. 17A-B in an extended configuration.

DETAILED DESCRIPTION

Figure 1:
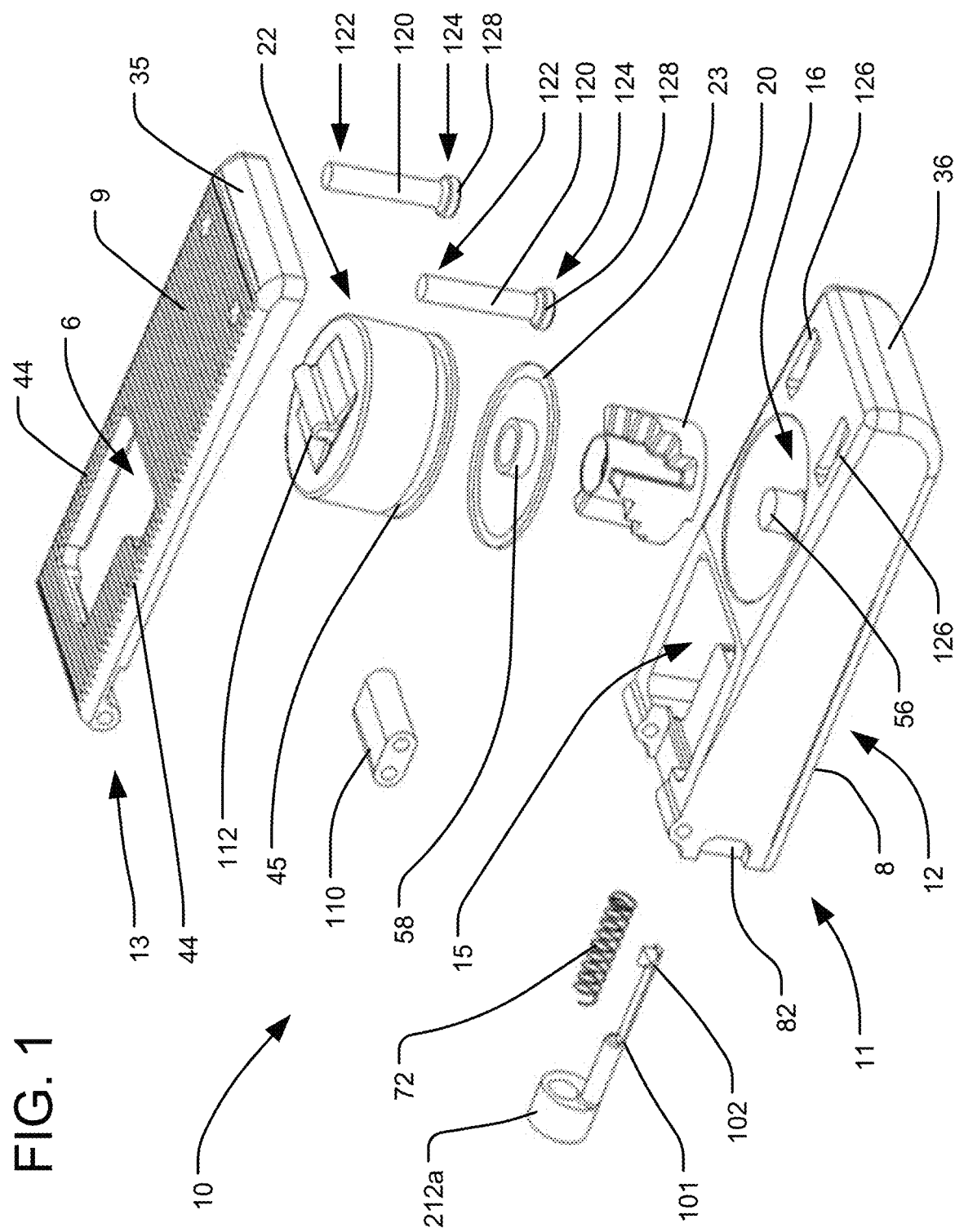
FIG. 1 is an exploded, perspective view of an implant in accordance with one embodiment of the present invention.
Figure 2A:
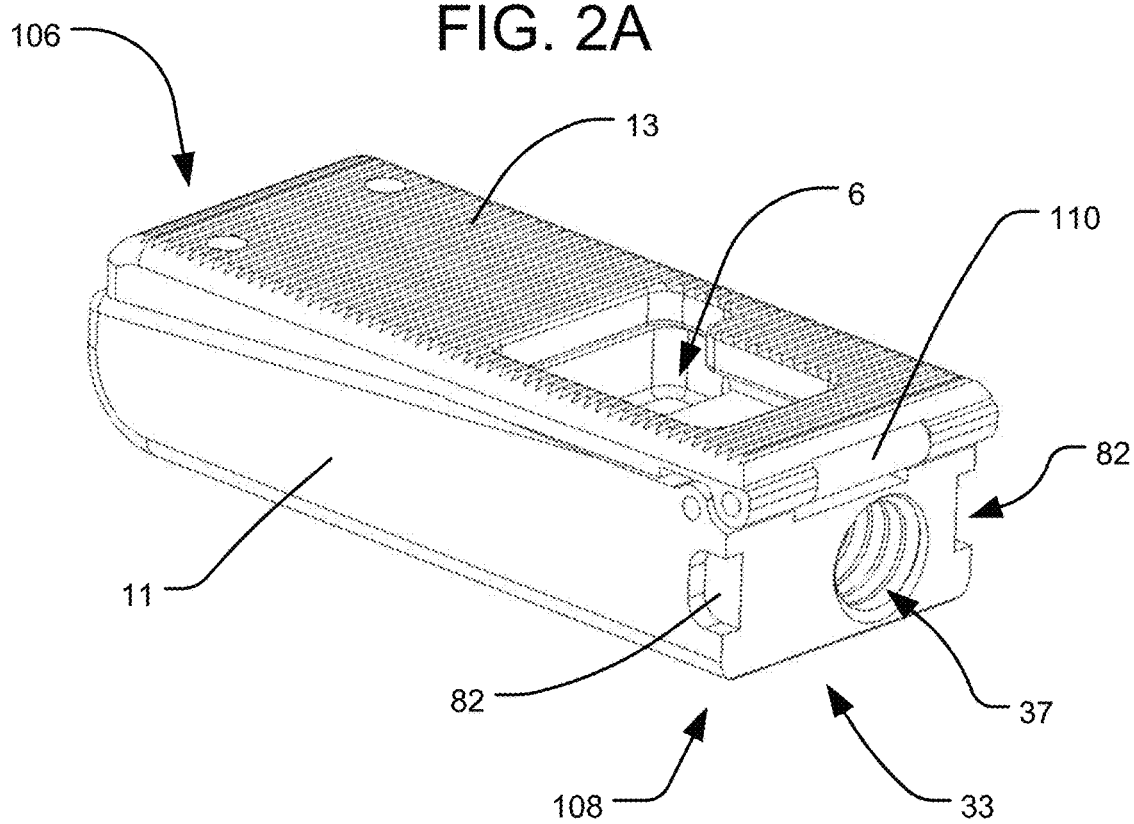
FIGS. 2A-B are perspective views of the embodiment of the implant of FIG. 1 in a contracted configuration.
Figure 2B:
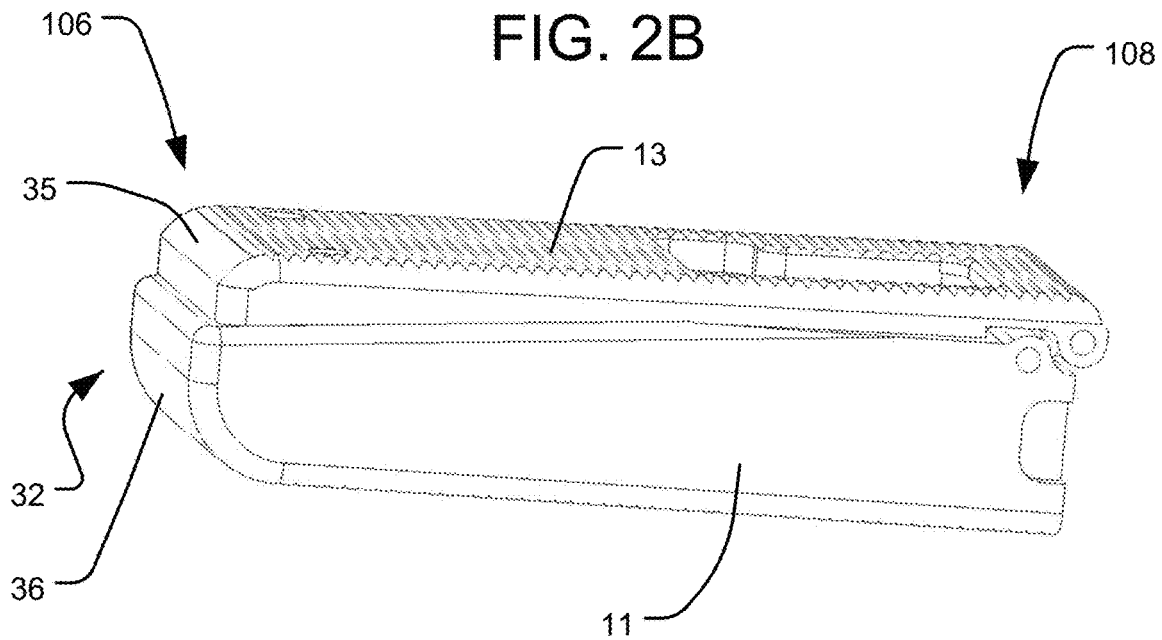
Figure 3A:
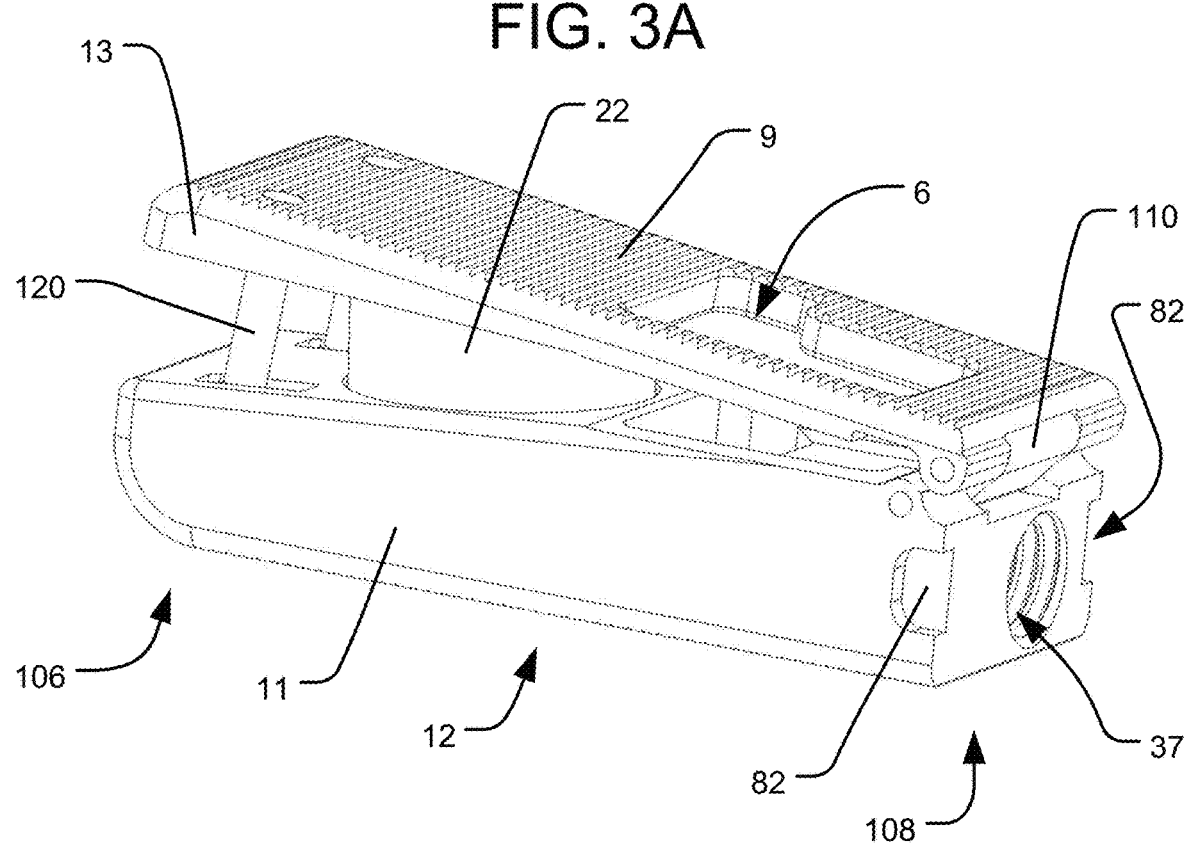
FIGS. 3A-B are perspective views of the embodiment of the implant of FIG. 1 in an extended configuration.
Figure 3B:
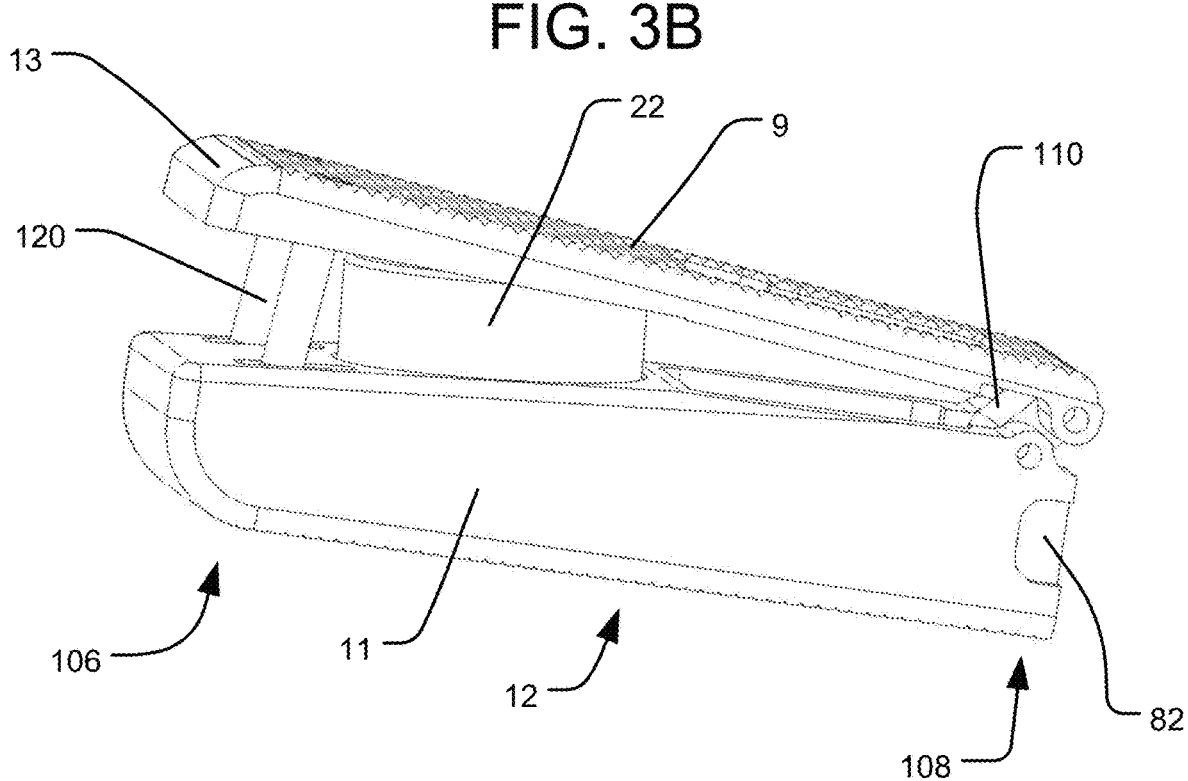

FIGS. 1-8B illustrate an embodiment of an intervertebral implant 10 in accordance with the present invention. The implant 10 generally includes a housing 11 and a top end plate 13, and the housing defines an interior cavity 15 within it. The top end plate 13 may include an opening 6 within it, bounded by connecting members or struts 44 extending between the proximal and distal sides of the top end plate 13, which opening 6 communicates with the interior cavity 15. The bottom 12 of the housing 11 may also include one or more openings 7 within it, which openings communicate with the interior cavity 15, as shown in FIGS. 5A-6B. The bottom 12 of the housing 11 has a bottom end surface 8 and the top end plate 13 has a top end surface 9. The top end plate 13 is movably connected to the housing 11 on the opposite side of the housing 11 from the bottom end surface 8. The top and bottom end surfaces are the bone engaging surfaces of the implant, for engaging vertebrae above and below the implant when placed into the patient. Moreover, the implant 10 is expandable by moving the top end plate 13 away from the housing 11, from the contracted configuration illustrated in FIGS. 2A-B to the extended configuration illustrated in FIGS. 3A-B.

The implant 10 includes at least one extendable support element in the form of a piston 22 attached to the underside of the top end plate 13, which piston 22 is slidably received within a corresponding cylinder 16 defined within the housing 11. The sliding of the piston 22 along the cylinder 16 results in the movement of the top end plate away from the housing 11. The piston 22 and cylinder 16 may operate as part of a hydraulic system, in which the sliding of the piston 22 away from the bottom of the cylinder is driven by pressurized fluid within the cylinder 16, as discussed in the '620 Patent and the '854 Application. A seal member 23, which may be in the form of an o-ring, is positioned so as to seal the sliding interface between the cylinder 16 and the piston 22, in order to prevent the pressurized fluid from escaping through that interface. The seal member 23 may be seated within a corresponding groove 45 defined in the outer surface of the piston 22. In an alternative (not shown), the seal member 23 may be seated within a corresponding groove defined in the outer surface of the cylinder 16 abutting the piston 22, as disclosed in embodiments of the '854 Application.

Figure 5A:
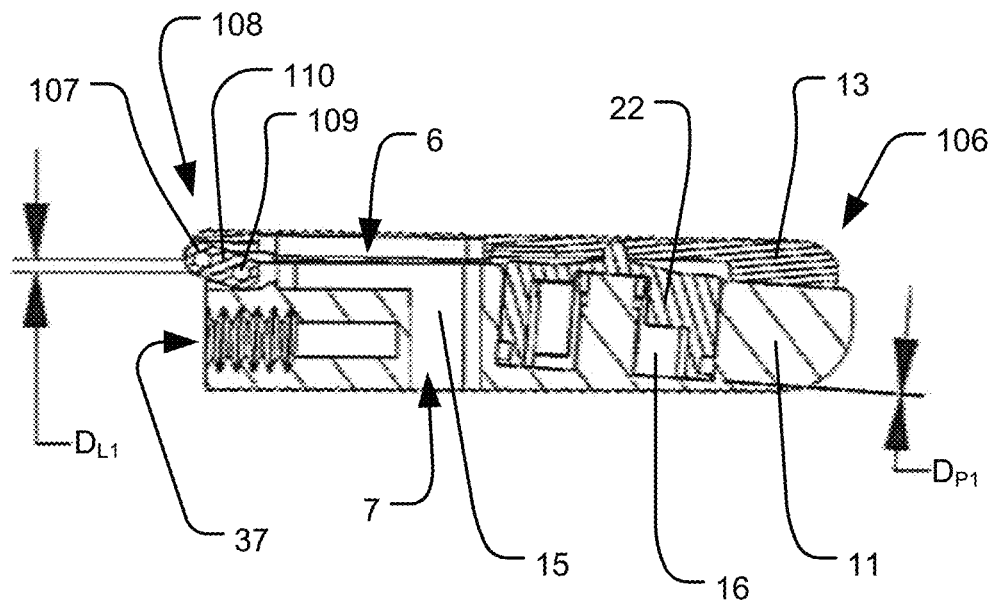
FIG. 5A is a cross-sectional side elevation view of the embodiment of the implant of FIG. 1 in a contracted configuration.
Figure 5B:
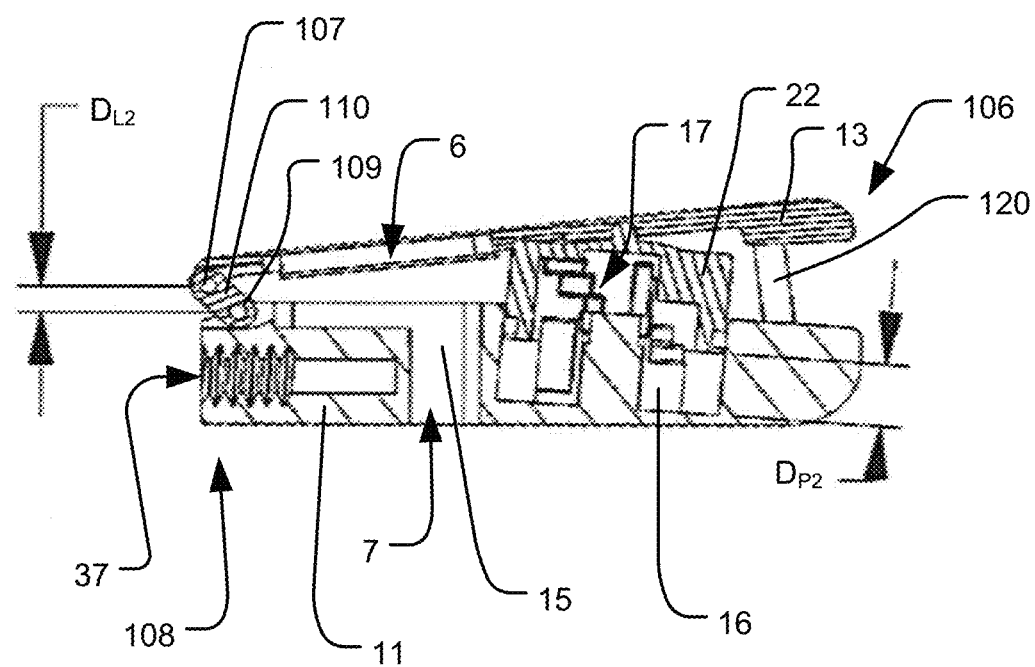
FIG. 5B is a cross-sectional side elevation view of the embodiment of the implant of FIG. 1 in an extended configuration.
Figure 7:
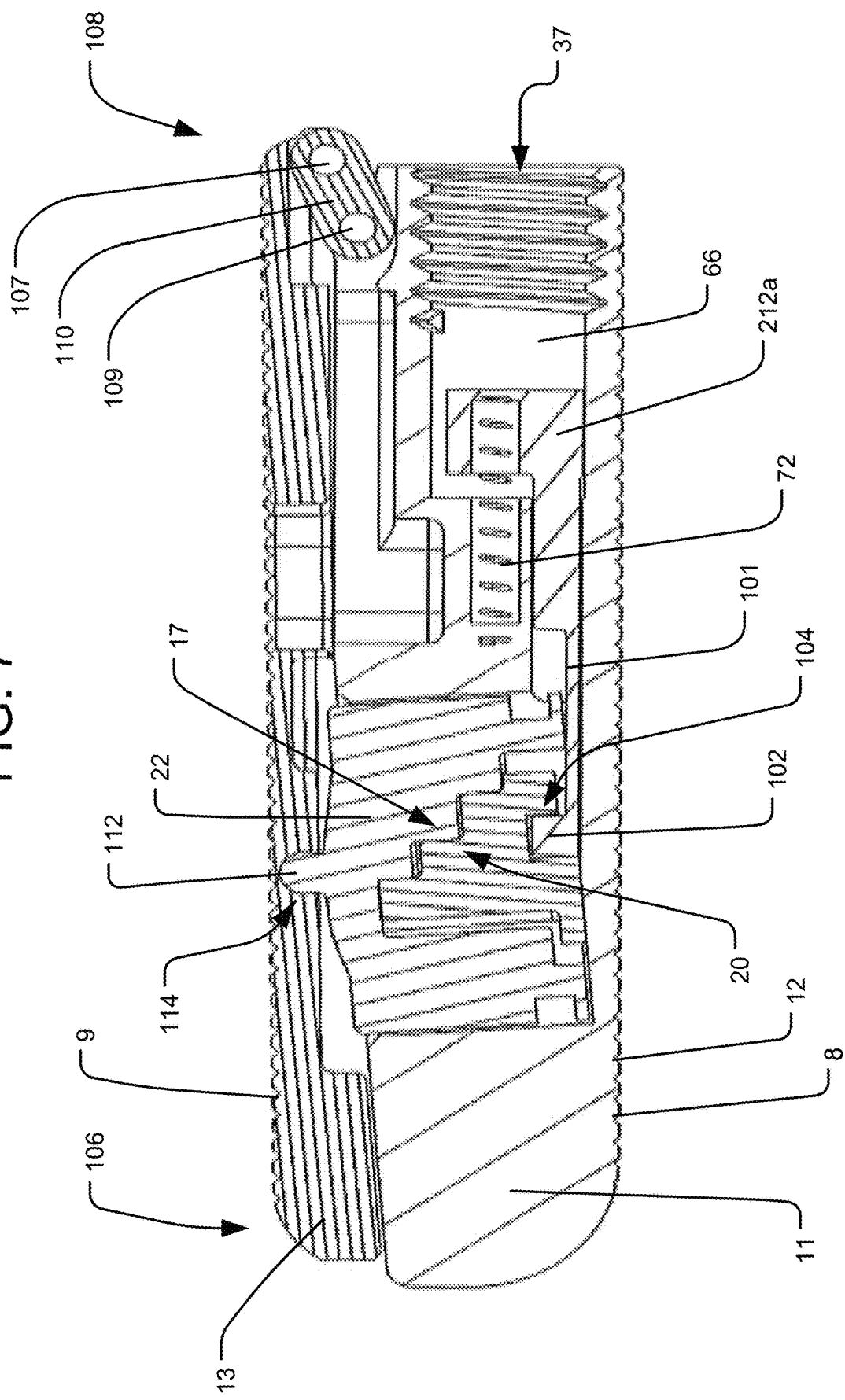
FIG. 7 is a cross-sectional side elevation view of the embodiment of the implant of FIG. 1 in a contracted configuration.
Figure 8A:
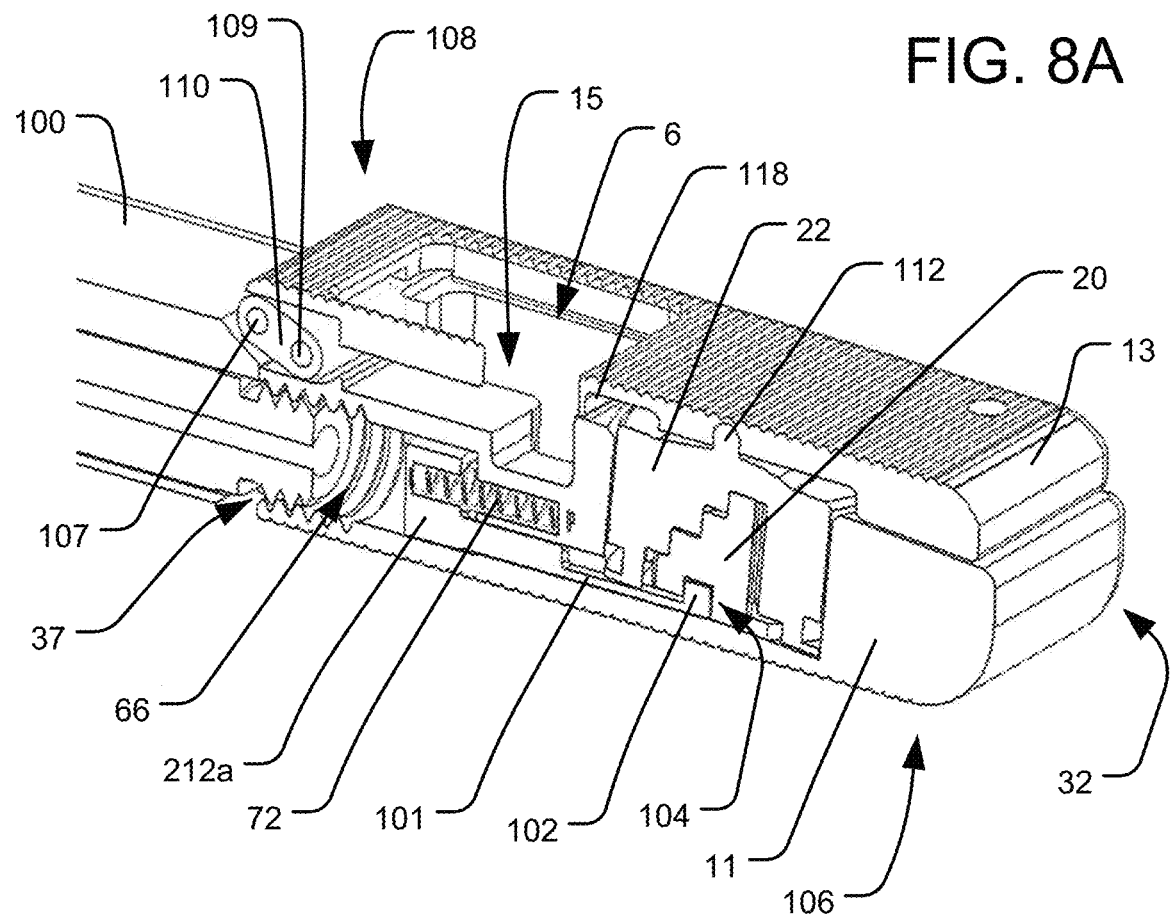
FIG. 8A is a perspective, cross-sectional view of the embodiment of the implant of FIG. 1 in a contracted configuration, connected to the delivery tool.
Figure 8B:
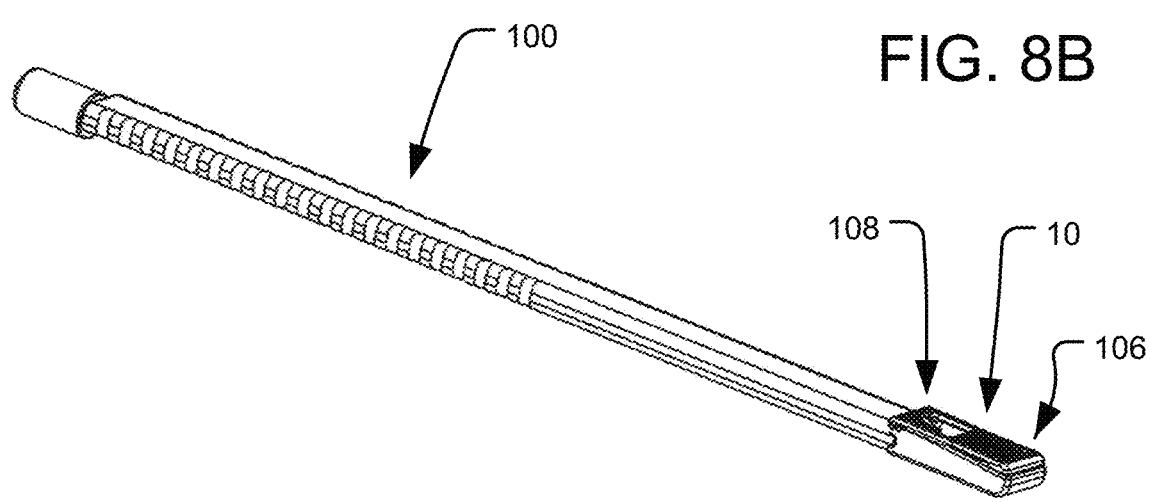
FIG. 8B is a perspective view of the embodiment of the implant of FIG. 1 in a contracted configuration, connected to the delivery tool.
Figure 11A:
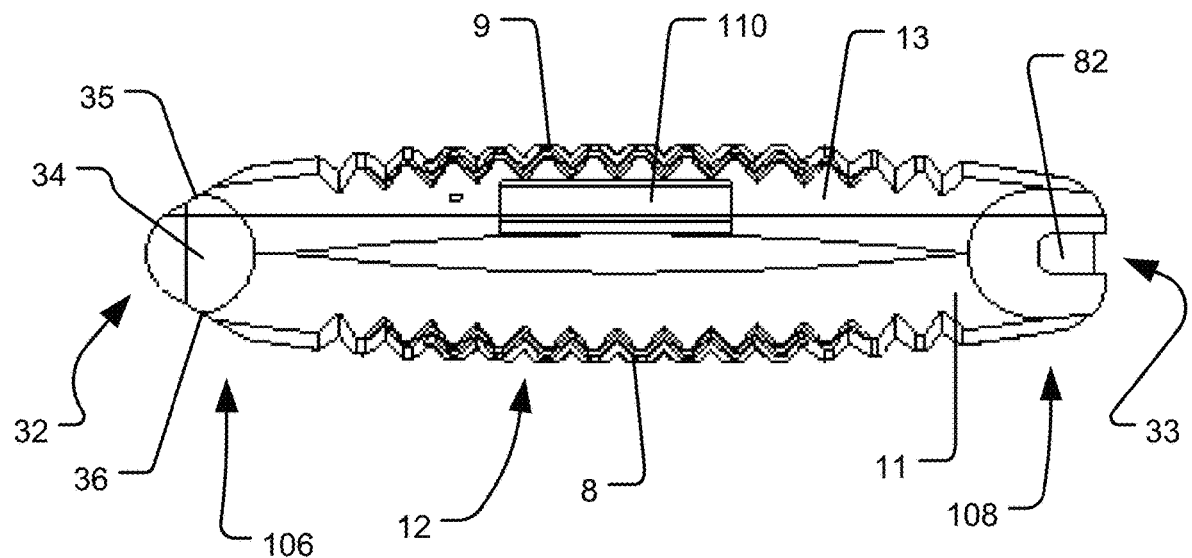
FIG. 11A is a side elevation view of the embodiment of the implant of FIG. 9A in a contracted configuration.
Figure 11B:
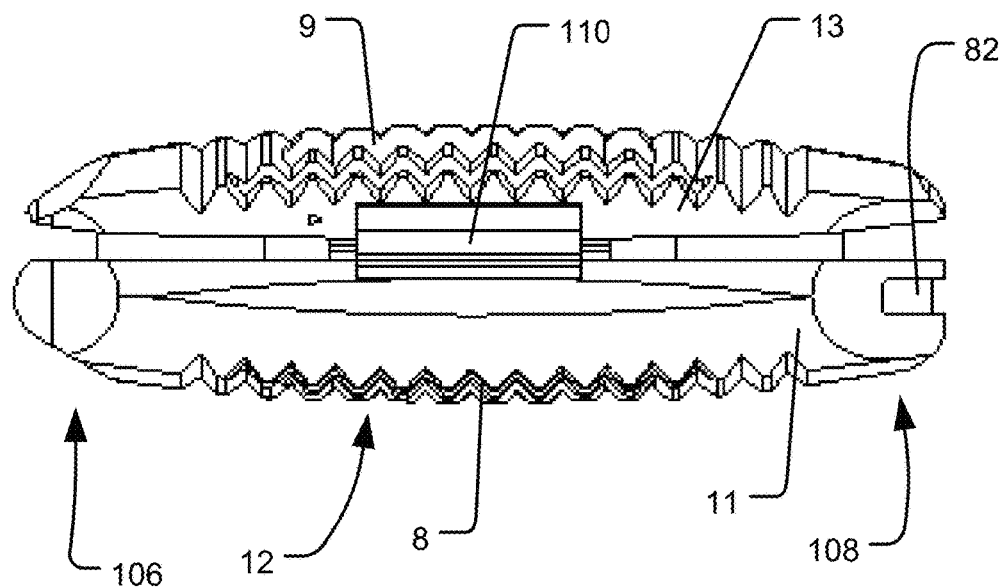
FIG. 11B is a side elevation view of the embodiment of the implant of FIG. 9A in an extended configuration.
Figure 12A:
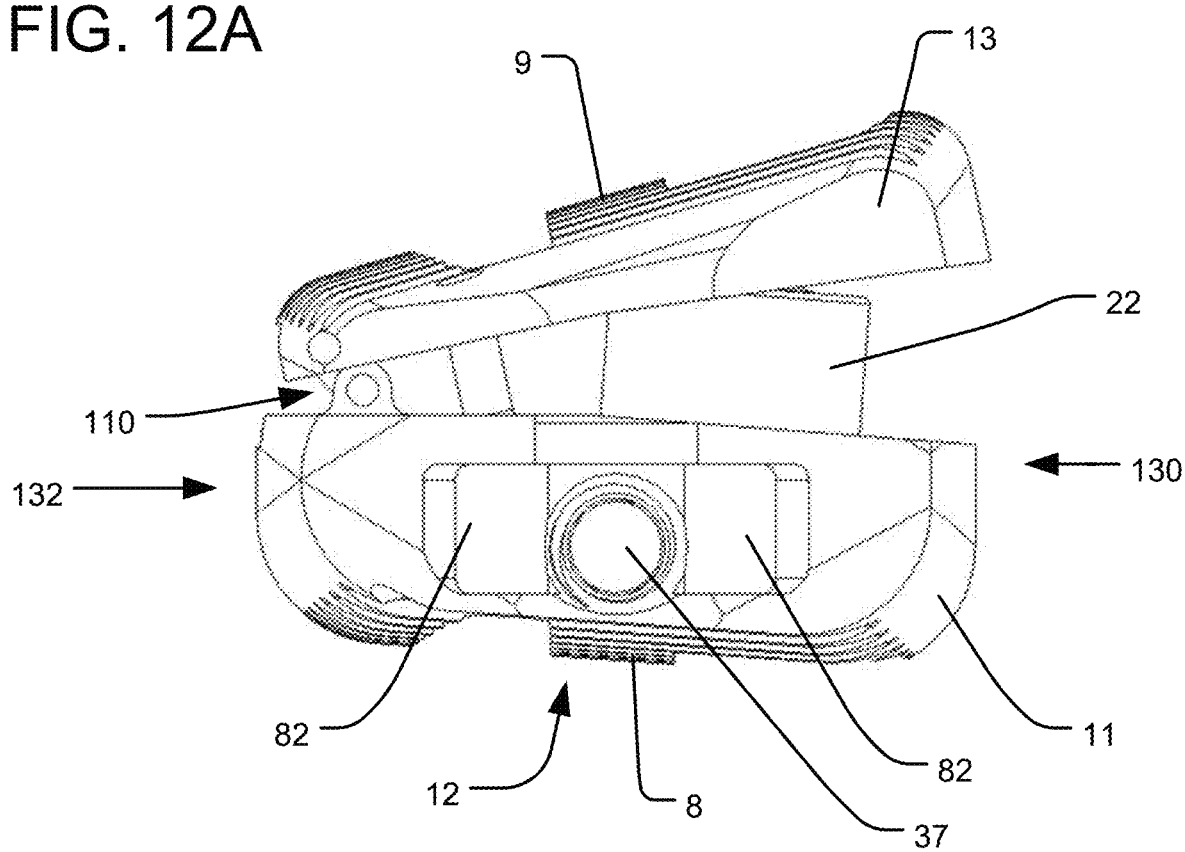
FIG. 12A is a rear elevation view of the embodiment of the implant of FIG. 9A in an extended configuration.
Figure 12B:
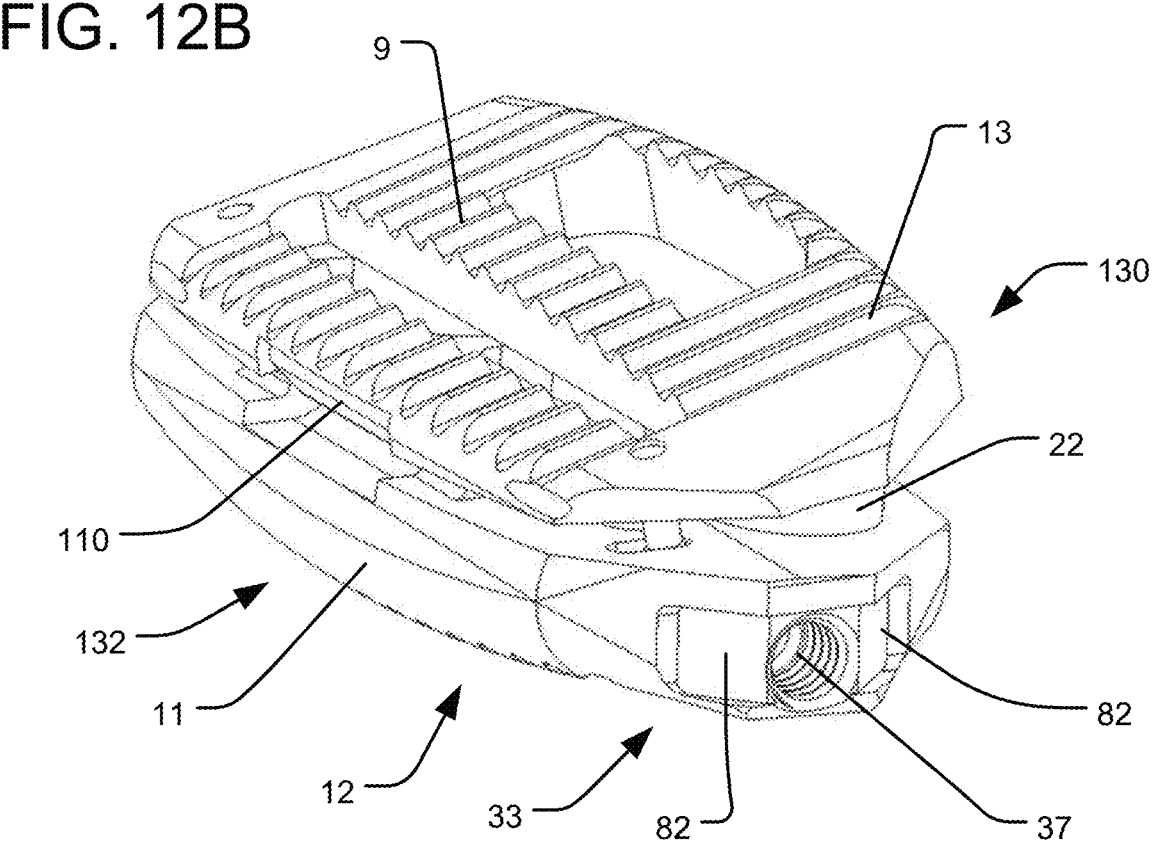
FIG. 12B is a perspective view of the embodiment of the implant of FIG. 9A in an extended configuration.

The implant 10 also includes a locking system to lock the position of the top end plate 13 by preventing the top end plate 13 from translating back towards the housing 11. That locking system may include inter-engaging locking elements. For example, the implant 10 may include a lower lock support 20 positioned within the housing 11 and a corresponding upper lock support 17 (see FIGS. 5B and 7) connected to the underside of the top end plate 13. As shown in FIGS. 5B and 7, the upper lock support 17 may be positioned within and fixed with respect to the piston 22. Indeed, the upper lock support 17 may be integrally formed with the piston 22. The structure and operation of components of suitable locking systems, including the operation of the upper and lower lock supports 17, 20, are further described in the '620 Patent and the '854 Application. For example, as disclosed in the '854 Application, the lower lock support 20 is rotatably received about an axle 56 mounted within the cylinder 16, and a bushing 58 may be provided at the top end of the axle 56 to constrain the axial position of the lower lock support 20 with respect to the axle 56. Additionally, as disclosed in the '620 Patent, and as illustrated in FIGS. 7 and 8A herein, the implant may include a pushable unlocking tether 212a engaged with lower lock support 20 so as to rotate the lower lock support 20 in the unlock direction when the unlocking tether 212a is pushed in the distal direction. For example, the distal end of the unlocking tether 212a may have an extension 101 having a laterally projecting tab 102 coupled with a receptacle 104 of the lower lock support 20 so as to rotate the lower lock support 20 about the axle 56. When the lower lock support 20 has thus been unlocked from the upper lock support 17, the top end plate 13 will be allowed to move back towards the housing 11, as disclosed in the '620 Patent. The unlocking tether 212a may be biased in the proximal direction by a linear spring 72, so as to bias the lower lock support 20 into locking engagement with the upper lock support 17 when the unlocking tether 212a is not being depressed.

As disclosed in the '854 Application, the housing 11 may include a channel 66 formed within it, which may serve as a pressure channel for delivering a pressurized fluid (e.g., saline) to the interior of the cylinder 16 in order to drive the movement of the piston 22 to expand the implant. As shown in FIGS. 7 and 8A herein, the unlocking tether 212a may be positioned in the pressure channel 66. In alternative embodiments (not shown), the unlocking tether 212a may be positioned in a distinct channel within the housing 11 from the pressure channel 66 that delivers the hydraulic fluid.

The implant 10 preferably defines a leading nose 32 at a distal end 106 of the implant and an engagement region 33 at a proximal end 108 of the implant. The leading nose 32 may have a top tapered and/or rounded face 35 and a bottom tapered and/or rounded face 36. The leading nose 32 may additionally include inwardly directed side tapered and/or rounded faces (not shown). The tapered and/or rounded faces 35, 36 of the leading nose enable non-traumatic insertion of the implant 10 past neural elements and between vertebral bodies. The distal end may also include structures that aid in manipulating the implant in situ (e.g., steering elements that facilitate at least partial rotation of the implant). The engagement region 33 includes a delivery tool anchor 37, which may be in the form of a threaded bore, that allows secure attachment of the implant 10 to a delivery tool 100, such as one illustrated in U.S. Pat. Nos. 8,070,813; 8,998,924; 9,028,550 (hereinafter "the '550 Patent"); U.S. Provisional Patent Application No. 62/319,460 filed on Apr. 7, 2016, entitled Surgical Insertion Instruments (hereinafter "the '460 Application"); or U.S. patent application Ser. No. 15/480,781 filed on Apr. 6, 2017, entitled Surgical Insertion Instruments (hereinafter "the '781 Application"), the disclosures of all of which are hereby incorporated by reference herein as if fully set forth herein. The engagement region 33 also contains one or more of the pressure input ports for delivering a pressurized fluid to the interior of cylinder 16 in order to expand the implant 10. As illustrated in FIGS. 7 and 8A, the delivery tool anchor 37 may also serve as a pressure input port, by communicating with pressure channel 66. In such a configuration, the inserter may be structured such that the pressurized fluid is deliverable through the structure anchored to the delivery tool anchor 37. The engagement region 33 may also include one or more engagement features, such as a recess 82, which may be engageable by the delivery tool in order to act as an anti-rotation feature for securing the rotational orientation of the implant 10 with respect to the delivery tool anchor 37, as also disclosed in the '460 Application and the '781 Application.

Implant 10 is configured to be implanted between opposing vertebral bodies in the spine to facilitate bony fusion between those vertebral bodies. The implant 10 is shown in its collapsed or contracted configuration in FIGS. 2A-B and in one example of its expanded configuration in FIGS. 3A-B. In the collapsed state, the implant 10 can be inserted easily into the intervertebral body space through a minimal incision and with minimal tissue removal. Once in that space, the implant 10 can be expanded against the two opposing vertebral bodies to distract them and thereby restore height to the intervertebral space. This provides stable opposition of the implant 10 to both vertebral bodies and optimizes the bony fusion process. The fusion process can also be enhanced by filling the interior cavity 15 with autologous and/or allogeneic bone graft, a bone growth enabling matrix, and/or bone growth stimulating substances prior to and/or after insertion into the body.

The implant 10 is preferably configured such that there is differential expansion at each end of the implant. For example, as shown in FIGS. 3A-6B, the implant is structured such that the top end plate 13 moves further from the housing 11 at the distal end 106 of the implant than at the proximal end 108 of the implant. Desirably, there is still some expansion at the proximal end 108, however, and therefore the implant top end plate 13 is connected to the housing 11 at the proximal end 108 by a connecting member that permits such expansion. In the embodiment of FIGS. 1-8B, the connecting member is a linkage 110 pivotably connected to the top end plate 13 at a top end 107 of the linkage and pivotably connected to the housing 11 at a bottom end 109 of the linkage. Thus, when the top end plate 13 is driven away from the housing 11 by the outward translation of the piston 22, the linkage 110 rotates with respect to both the housing 11 and the top end plate 13 so as to guide the top end plate 13 away from the housing 11 along a defined path at the proximal end 108 of the implant 10, as shown in FIGS. 3A-6B. For example, as shown in the contracted configuration of FIG. 5A, the piston 22 may initially be spaced from the bottom of the cylinder 16 by a distance $D_{P1}$, and the vertical distance between the top and bottom ends 107, 109 of the linkage 110 is $D_{L1}$. Then, in an extended configuration, as illustrated in FIG. 5B, the distance from the piston 22 to the bottom of the cylinder 16 may be increased to $D_{P2}$, and the vertical distance between the top and bottom ends 107, 109 of the linkage 110 may be increased to $D_{L2}$. In one exemplary embodiment, $D_{P1}$ may be 0 mm, $D_{P2}$ may be 3 mm, $D_{L1}$ may be 0.62 mm, and $D_{L2}$ may be 1.26 mm. Thus, in such an embodiment, for an expansion of 3 mm at the piston end of the top end plate 13, the linkage provides for 0.64 mm of expansion at the proximal end 108 of the top end plate 13.

Figure 4A:
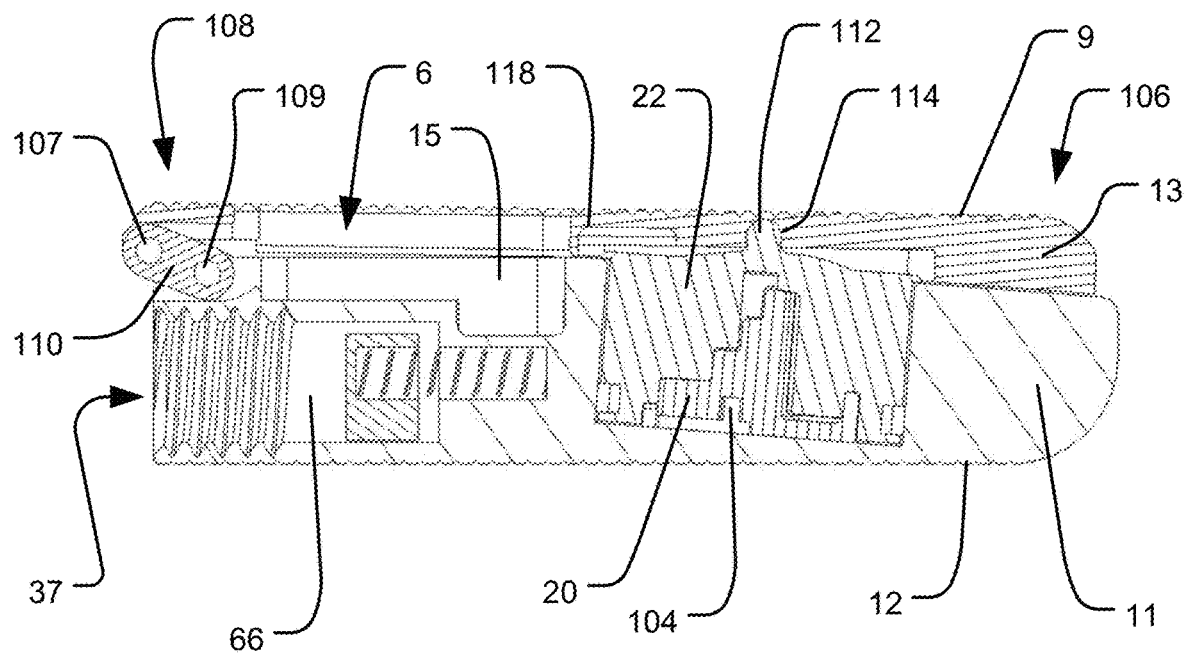
FIG. 4A is a cross-sectional side elevation view of the embodiment of the implant of FIG. 1 in a contracted configuration.
Figure 4B:
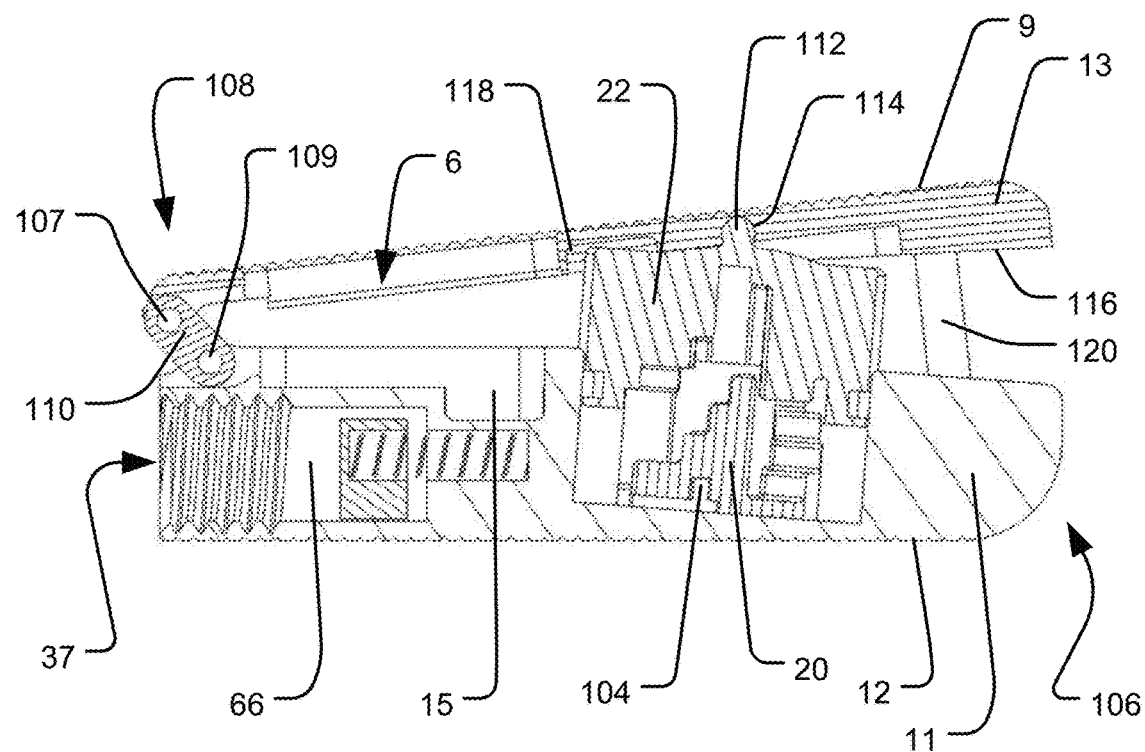
FIG. 4B is a cross-sectional side elevation view of the embodiment of the implant of FIG. 1 in an extended configuration.

In order to permit the top end plate 13 to rotate during expansion, the piston 22 may be connected to the top end plate 13 by a pivotable connection, such as a rotatable pin connection. For example, the top of the piston 22 may include a protruding fulcrum 112 shaped to be received within a corresponding recess 114 in the underside 116 of the top end plate 13. The top end plate 13 may also include at least one relief 118 in its underside 116 to provide clearance for part of the piston 22 during expansion, as shown in FIGS. 4A-B and 8A.

Figure 6A:
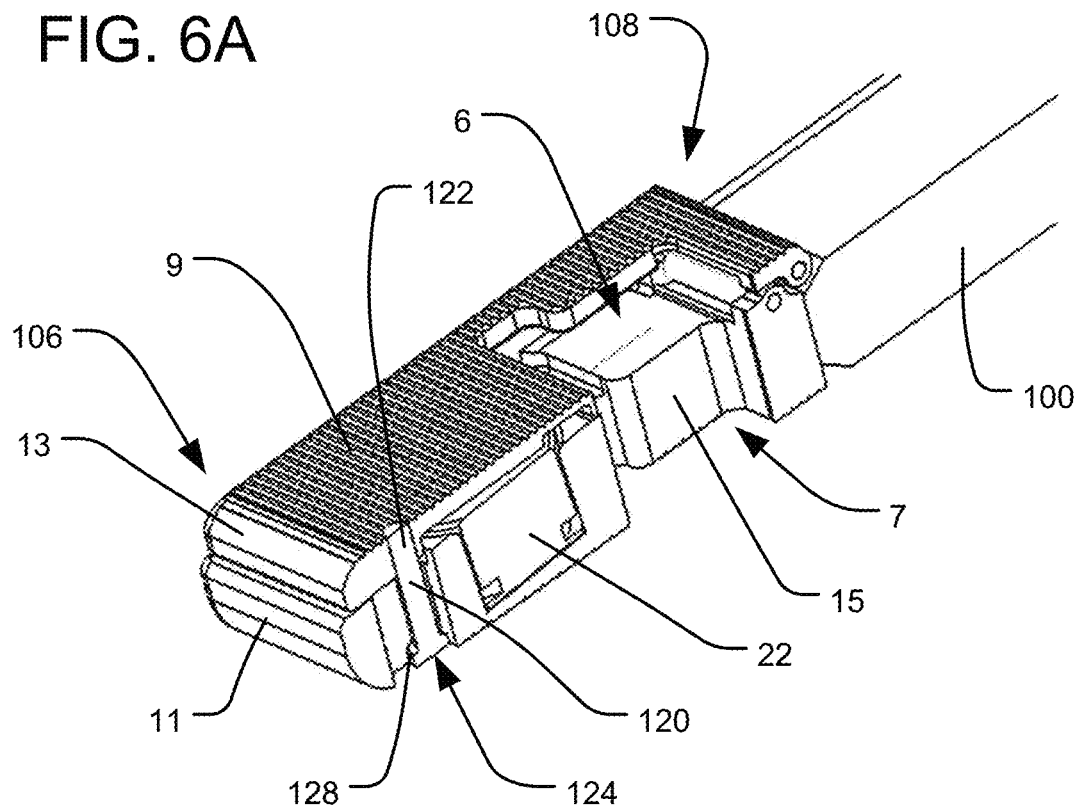
FIG. 6A is a perspective, cross-sectional view of the embodiment of the implant of FIG. 1 in a contracted configuration, connected to a delivery tool.
Figure 6B:
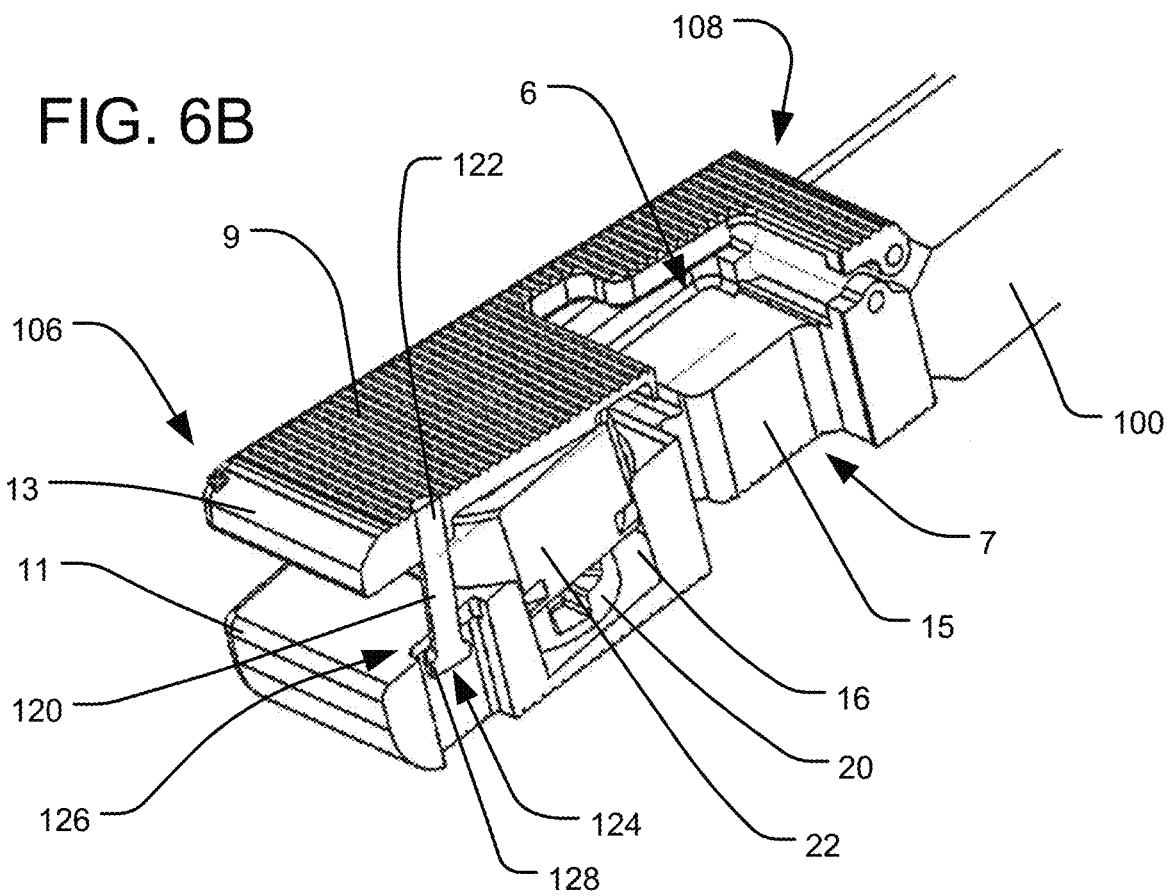
FIG. 6B is a perspective, cross-sectional view of the embodiment of the implant of FIG. 1 in an extended configuration, connected to the delivery tool.

The implant 10 may include a stop member to constrain the maximum expansion of the implant. For example, as shown in FIGS. 6A-B, at least one post 120 may be connected at a top end 122 to the top end plate 13 such that the bottom end 124 of the post 120 is received by the housing 11. The post 120 may be slidably received through a slot 126 in the housing 11, and an enlarged portion 128 having a larger dimension than the slot 126 may be provided on the bottom end 124 of the post 120, so as to stop further expansion of the implant when the enlarged portion 128 engages the slot 126, as shown in FIG. 6B. As shown in FIG. 1, two such posts 120 (with two corresponding slots 126) may be provided in some embodiments.

In embodiments of the invention, the extendable support element may deviate from being perpendicular to the top and bottom end surfaces 9, 8 when the implant 10 is in the contracted configuration. For example, as shown in FIGS. 4A-8A, the piston 22 and corresponding cylinder 16 may be angled at least slightly towards the distal end 106 of the implant 10. Desirably, angling the piston 22 and cylinder 16 in that manner may space the bottom of the cylinder 16 at its proximal end further away from the bottom end surface 8 of the housing 11 than at the distal end of the cylinder 16. That additional space at the proximal end of the cylinder 16 is preferably sufficient for the extension 101 of the unlocking tether 212a to pass between the bottom of the cylinder 16 and the bottom end surface 8 of the housing, such that the extension 101 can control the rotation of the lower lock support 20, as discussed above. By angling the cylinder 16 to achieve that space for the extension 101 rather than spacing the entire bottom of the cylinder 16 the needed distance, the overall height of the implant 10 may be desirably minimized Moreover, by angling the cylinder 16 in that manner, the movement of the piston 22 during expansion will have at least some horizontal component, which will desirably force the linkage 110 to rotate during expansion, thus providing the desired expansion at the proximal end 108 of the implant 10.

The above-described embodiment illustrated in FIGS. 1-8B is desirably structured to be used in a PLIF technique. That is, the generally linear shape of the implant between the distal 106 and proximal 108 ends of the implant may be particularly suitable for inserting two such implants into an intervertebral space (one on either side of the spine) along a posterior to anterior direction, such that the distal end 106 of the implant 10 is positioned more anteriorly with respect to the spine than the more posteriorly positioned proximal end 108 of the implant. Desirably, the differential expansion discussed above, when used in such a PLIF technique, allows for lordosis correction. That is, by providing expansion at the distal end 106 of the implant 10 (i.e., at the anterior portion of the spine), desirably the anterior portion of the spinal column will be lifted to correct lordosis. Moreover, by providing some expansion at the proximal end 108 of the implant (i.e., at the posterior portion of the spine), although less than at the anterior portion, the posterior portion of the spine will receive some lifting in order to decompress nerve roots. By providing a connecting member (e.g., linkage 110) at the proximal end 108 of the implant to control the expansion of the implant at the proximal end, as discussed above, the differential expansion at both the proximal and distal ends of the implant can be driven by a single input, such as one or more extendable support elements controlled by the same source (e.g., a single source of pressurized hydraulic fluid). Thus, benefits of such a configuration include a structure which is relatively simple to manufacture and which is simple to operate by a surgeon to achieve the desired lordosis- correcting expansion.

Mechanisms similar to those discussed above for providing differential expansion of the anterior and posterior portions of the spinal column can also be included in implants structured to be used in a TLIF technique or along a lateral approach. For example, an implant structured to be used in a lateral approach is illustrated in FIGS. 9A-12B. The same reference numerals used in FIGS. 1-8B in connection with components of the PLIF implant discussed above are used to indicate similar components in the lateral implant of FIGS. 9A-12B.

For example, the embodiment of FIGS. 9A-12B similarly includes a top end plate 13 and a housing 11 defining an interior cavity 15 within it. As shown in FIGS. 9A-10A, the implant 10 may include two such interior cavities 15, although more or fewer such cavities may be provided. The top end plate 13 may include openings 6 within it, bounded by connecting members or struts 44 extending between the proximal and distal sides of the top end plate 13, which openings 6 communicate with the respective interior cavities 15. The bottom 12 of the housing 11 may also include one or more openings 7 within it, which openings also communicate with the interior cavities 15. The bottom 12 of the housing 11 has a bottom end surface 8, and the top end plate 13 has a top end surface 9. The top end plate 13 is movably connected to the housing 11 on the opposite side of the housing 11 from the bottom end surface 8. The implant 10 is expandable by moving the top end plate 13 away from the housing 11 from the contracted configuration illustrated in FIGS. 9A and 10B-11A to the extended configuration illustrated in FIGS. 11B-12B.

In contrast to the embodiment illustrated in FIGS. 1-8B, two extendable support elements are illustrated in the embodiment of FIGS. 9A-12B, although other embodiments of a lateral implant may include one extendable support element or more than two extendable support elements. In the lateral embodiment of FIGS. 9A-12B, the extendable support elements may include pistons 22 slidably received within corresponding cylinders 16. The pistons 22 may both be driven by a pressurized fluid delivered through a channel 66 as discussed above and in the '854 Application. The implant 10 may also include a locking system having inter-engaging locking elements, which locking elements may also be unlockable to allow the top end plate 13 to move back towards the housing 11, as discussed above. For example, the locking elements may be interconnected so as to be simultaneously unlockable, as disclosed in the '854 Application and in the '620 Patent. As shown in FIG. 9B, the extension 101 of the unlocking tether 212a may be elongated so as to extend between both lower lock supports 20, and two laterally projecting tabs 102 may be provided to couple with both lower lock supports 20 so as to simultaneously rotate them about the corresponding axles 56.

The implant 10 preferably defines a leading nose 32 at a distal end 106 of the implant and an engagement region 33 at a proximal end 108 of the implant. The leading nose 32 may have a top tapered and/or rounded face 35 and a bottom tapered and/or rounded face 36. The leading nose 32 may additionally include inwardly directed side tapered and/or rounded faces 34. The engagement region 33 includes a delivery tool anchor 37 for secure attachment of the implant 10 to a delivery tool 100, as discussed above. The engagement region 33 may also include one or more engagement features, such as one or more recesses 82, which may be engageable by the delivery tool in order to act as an anti-rotation feature for securing the rotational orientation of the implant 10 with respect to the delivery tool anchor 37. The engagement region 33 may also contain one or more of the pressure input ports for delivering a pressurized fluid to the interior of cylinder 16 in order to expand the implant 10.

As with the embodiment of FIGS. 1-8B, the lateral implant 10 of FIGS. 9A-12B may be configured to produce differential expansion at opposing ends of the implant. Since the lateral embodiment of FIGS. 9A-12B is desirably inserted laterally into the disc space between two vertebral bodies, the differential expansion may be between the opposing ends of the implant on either side of the longitudinal axis, rather than between the proximal 108 and distal 106 ends of the implant. In that regard, the lateral implant is desirably positioned in the spine such that one of those ends is an anterior end 130 of the implant and the other end is a posterior end of the implant 132. Thus, like the embodiment of FIGS. 1-8B, the embodiment of FIGS. 9A-12B may allow for lordosis correction by providing expansion at both the anterior and posterior ends of the implant, with the anterior end 130 expanding by a greater amount than the posterior end 132. To accommodate that differential expansion, and the resulting rotation of the top end plate 13, the pistons 22 may be pivotably connected to the top end plate 13 by respective fulcrums 112, as in the embodiment of FIGS.

1-8B. Similarly, the top end plate 13 may be connected to the housing 11 at the posterior end 132 of the implant by a connecting member, such as by a rotatable linkage 110 pivotably connected to the top end plate 13 and the housing 11. Although not shown, the lateral embodiment of the implant 10 may also include one or more stop members to constrain the maximum expansion of the implant, as discussed above in connection with the PLIF embodiment. Moreover, the pistons 22 may be angled towards the anterior end 130 of the implant, as discussed in connection with the PLIF embodiment, which may allow a mechanism (such as a rack, as disclosed in the '854 Application) to pass between the bottom of the cylinders 16 and the bottom end surface 8 of the housing 11, so as to engage lower lock supports of the locking system.

An implant structured to be used in a TLIF technique (not shown) which similarly allows for differential expansion between the anterior 130 and posterior 132 ends of the implant 10 may also be provided in accordance with the present invention. Such an implant may generally be configured like the lateral implant of FIGS. 9A-12B, in that one or more extendable support elements may be provided on an anterior side of the longitudinal axis and a connecting member, such as a linkage 110, may be provided on the opposing, posterior side of the longitudinal axis. A primary difference between such a TLIF embodiment and the lateral embodiment discussed above may be that the longitudinal axis of the TLIF implant may be curved, rather than straight, such that the outer geometry of the implant has a curved, kidney bean-like shape between its proximal 108 and distal 106 ends. An exemplary outer geometry for such a TLIF implant is illustrated in the '854 Application.

In the embodiments of the implant 10 discussed above, the linkage 110 causes the top end plate 13 to rotate during the expansion induced by the extendable support elements. The top end plate 13 will thus have an instantaneous center of rotation spaced posteriorly from the implant 10, although the location of the instantaneous center of rotation will move during the expansion of the implant. As illustrated in FIG. 13, the greater the distance X that the center of rotation R of the top end plate 13 is spaced from the implant 10, the greater the posterior expansion Y will be. Thus, various geometries can be adjusted in order to create the desired amount of posterior expansion Y relative to the anterior expansion Z provided by the extendable support elements. For example, the length of the linkage 110 and its position within the implant 10 (i.e., where its top and bottom ends 107, 109 are connected to the top end plate 13 and to the housing 11, respectively) can be varied.

Figure 14A:
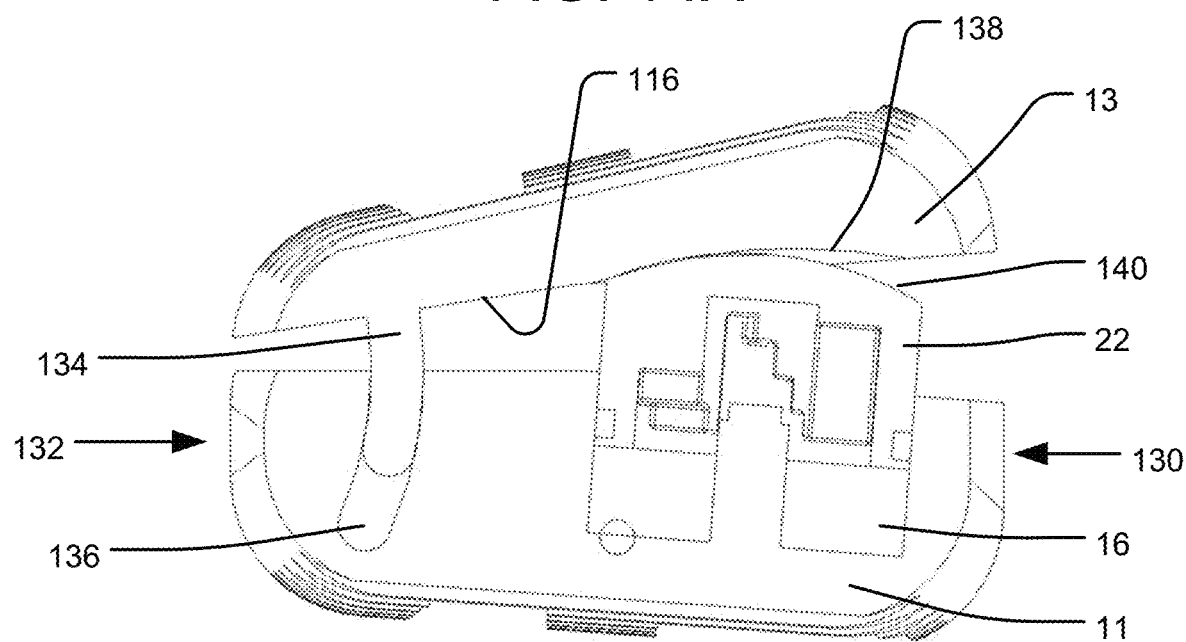
FIG. 14A is a cross-sectional rear elevation view of an implant in accordance with another embodiment of the present invention in an extended configuration.
Figure 14B:
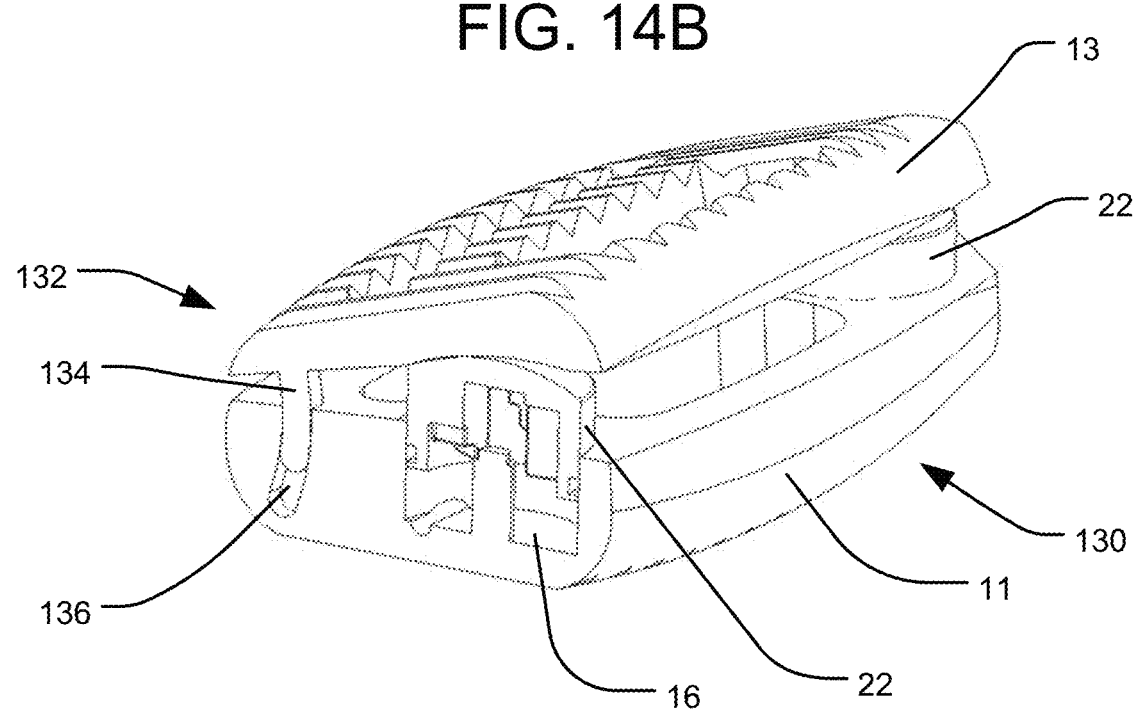
FIG. 14B is a perspective, cross-sectional view of the embodiment of the implant of FIG. 14A in an extended configuration.
Figure 15A:
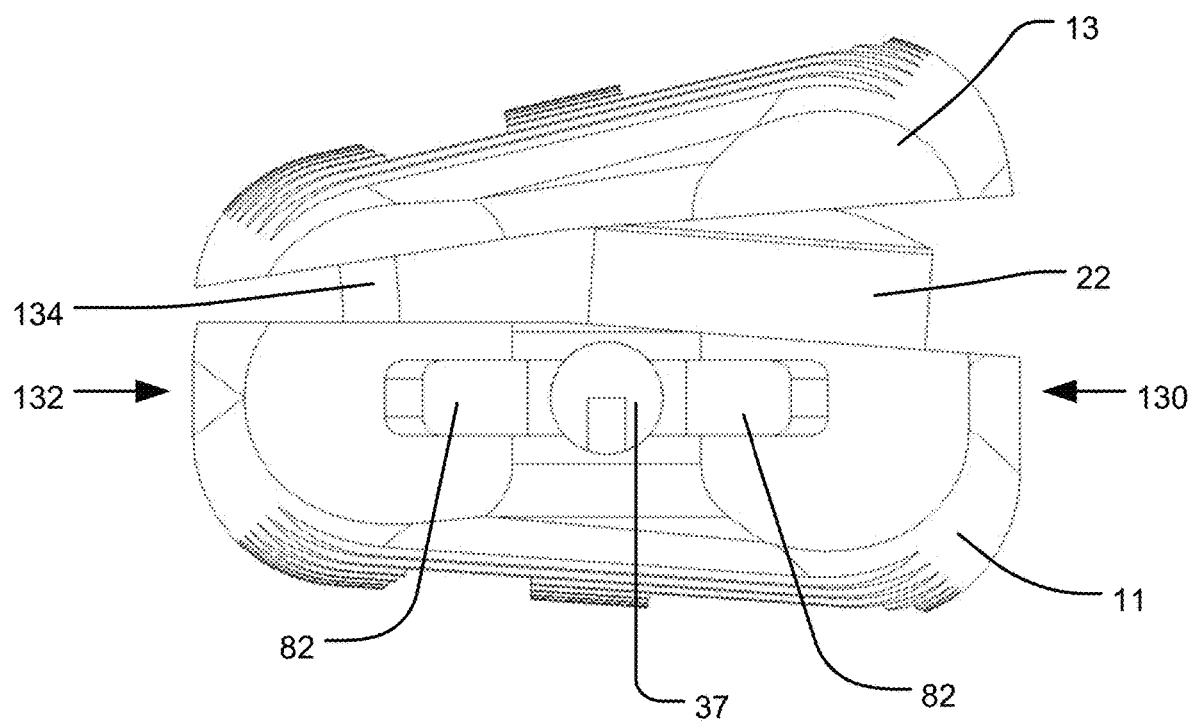
FIG. 15A is a rear elevation view of the embodiment of the implant of FIG. 14A in an extended configuration.
Figure 15B:
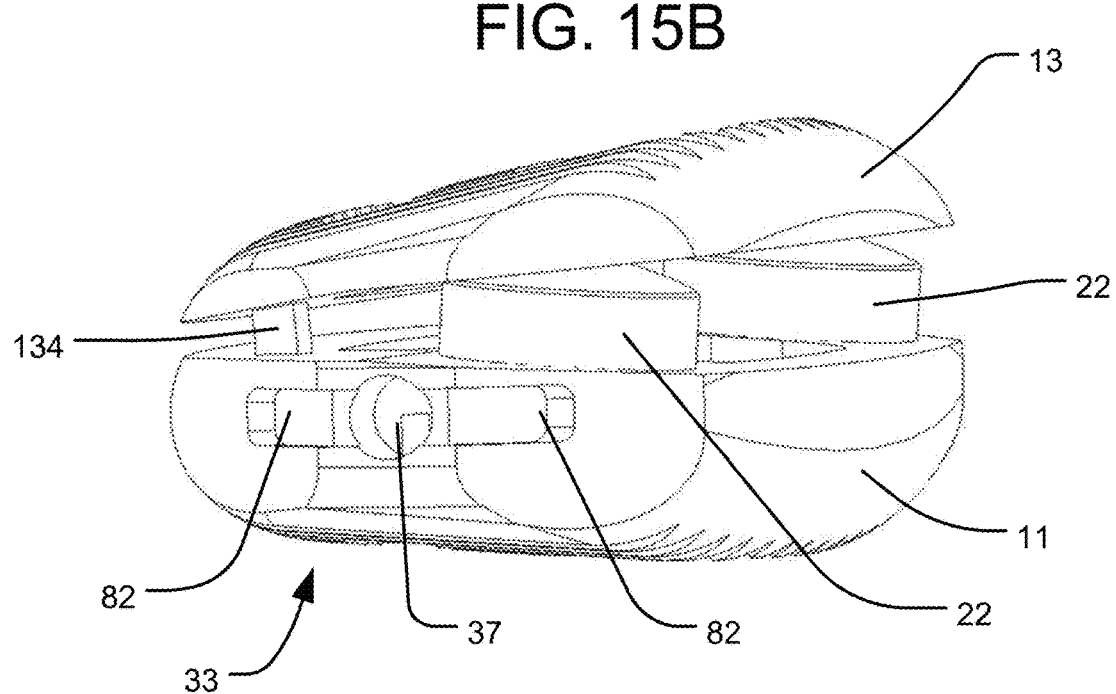
FIG. 15B is a perspective view of the embodiment of the implant of FIG. 14A in an extended configuration.

In other embodiments of an implant in accordance with the present invention, a posteriorly-spaced center of rotation can be provided by other mechanisms. For example, as shown in the exemplary embodiment of a lateral implant illustrated in FIGS. 14A-15B, the linkage 110 may be replaced by another connecting member in the form of an extension 134 slidably received within a track 136. As illustrated, the extension 134 may be rigidly connected to the top end plate 13 (e.g., either integrally formed with or rigidly secured to the top end plate 13) and slidably received within a track 136 in the housing 11. The extension 134 may have an arcuate shape, and the track 136 may have a matching arcuate shape, such that the top end plate 13 is constrained to follow a defined path when pushed outwardly by the extendable support elements (e.g., pistons 22). The arcuate shapes may of the extension 134 and track 136 may define a fixed radius, such that the center of rotation R of the top end plate 13 has a fixed location during expansion of the implant 10. In order to avoid over constraining the system, the pin connection of the embodiments of FIGS. 1-12B may be replaced with a slidable interface between the top of the pistons 22 and the underside 116 of the top end plate 13. For example, as shown in FIG. 14A, the underside 116 of the top end plate 13 may include concave surfaces 138, and the tops of the pistons 22 may include convex surfaces 140 shaped to slidably engage the respective concave surfaces 138 during expansion.

Although not shown, the embodiment of the implant illustrated in FIGS. 14A-15B may also include one or more stop members to constrain the maximum expansion of the implant, as discussed above. Moreover, in accordance with the present invention, the above-discussed mechanisms that connect the housing 11 to the top end plate 13 in order to provide differential expansion can also be used in embodiments of implants used in PLIF and TLIF techniques. For example, such PLIF and TLIF implants would be structured as discussed above, except that the linkages 110 would be replaced by extensions 134 slidably received within tracks 136, and the fulcrums 112 and corresponding recesses 114 may be replaced by concave and convex surfaces 138, 140 between the extendable support elements and the top end plate 13.

Figure 16A:
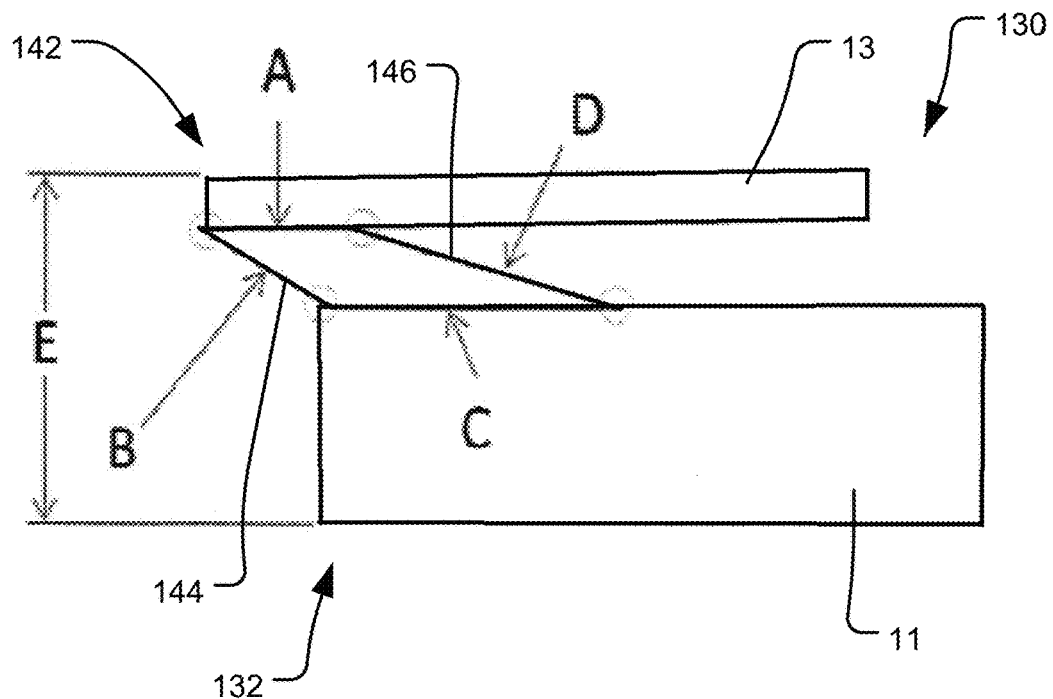
FIG. 16A is a schematic illustration of components of an implant in accordance with another embodiment of the present invention in a contracted configuration.
Figure 16B:
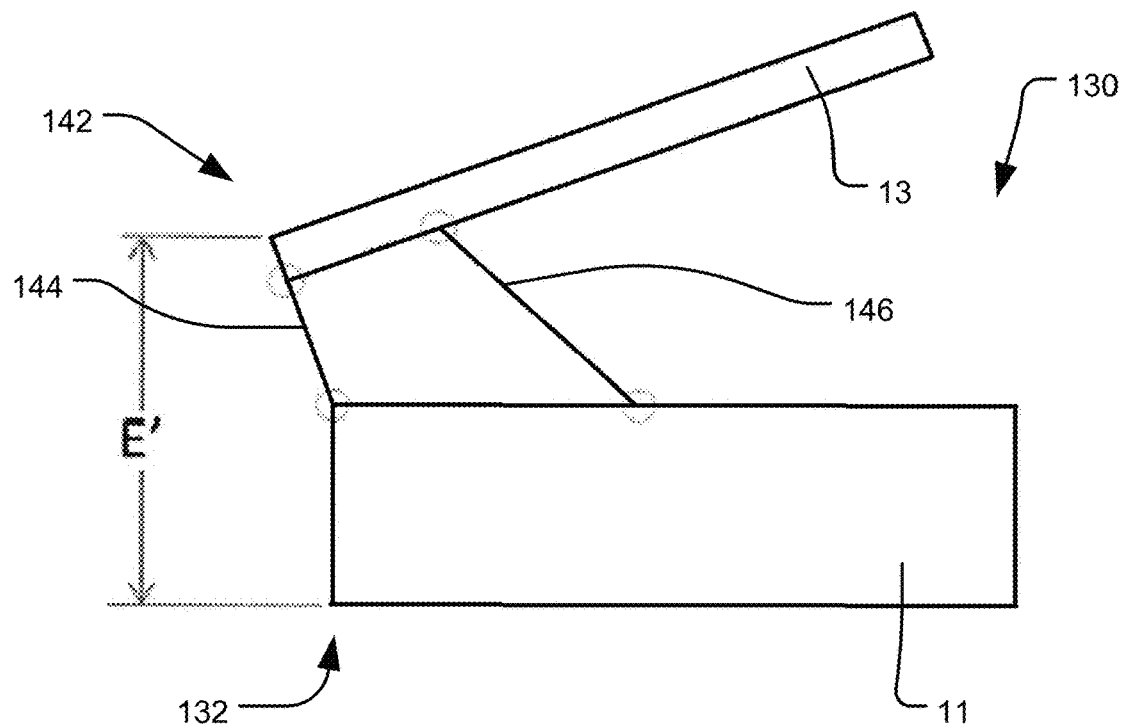
FIG. 16B is a schematic illustration of the components of the embodiment of the implant of FIG. 16A in an extended configuration.
Figure 17A:
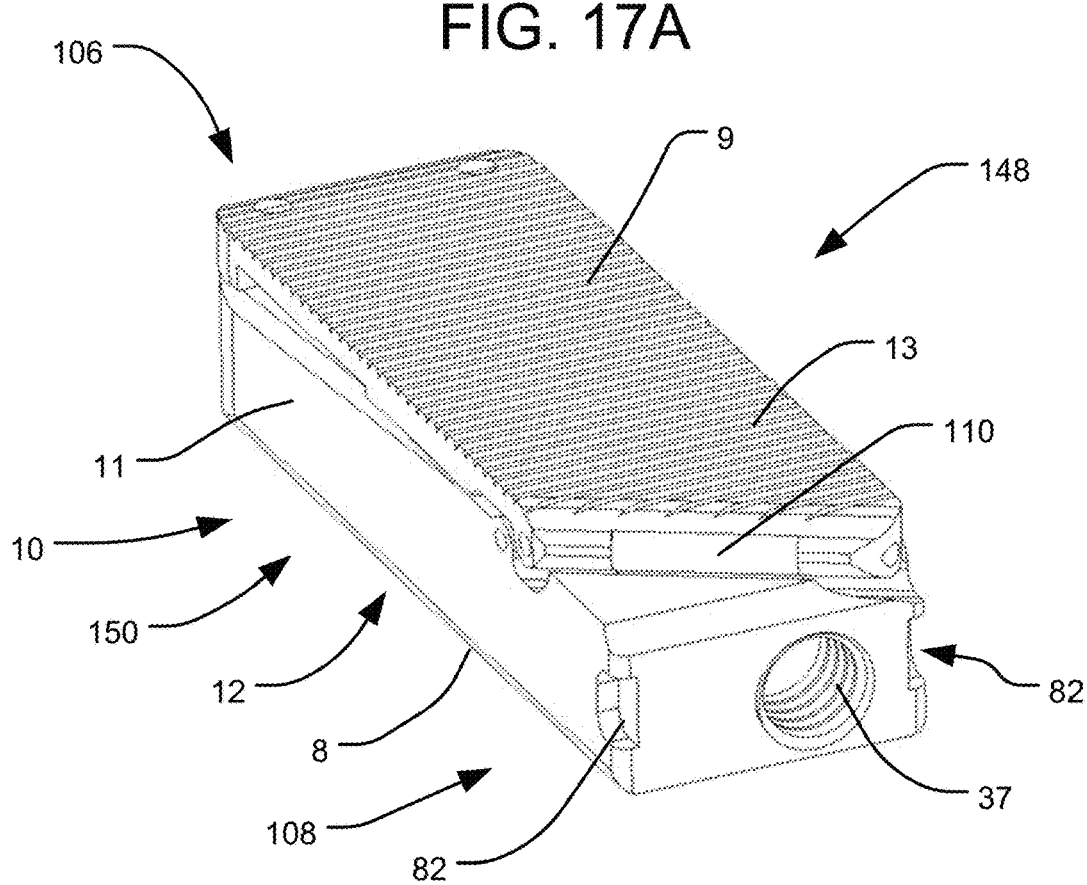
FIGS. 17A-B are perspective views of an implant in accordance with another embodiment of the present invention in a contracted configuration.
Figure 17B:
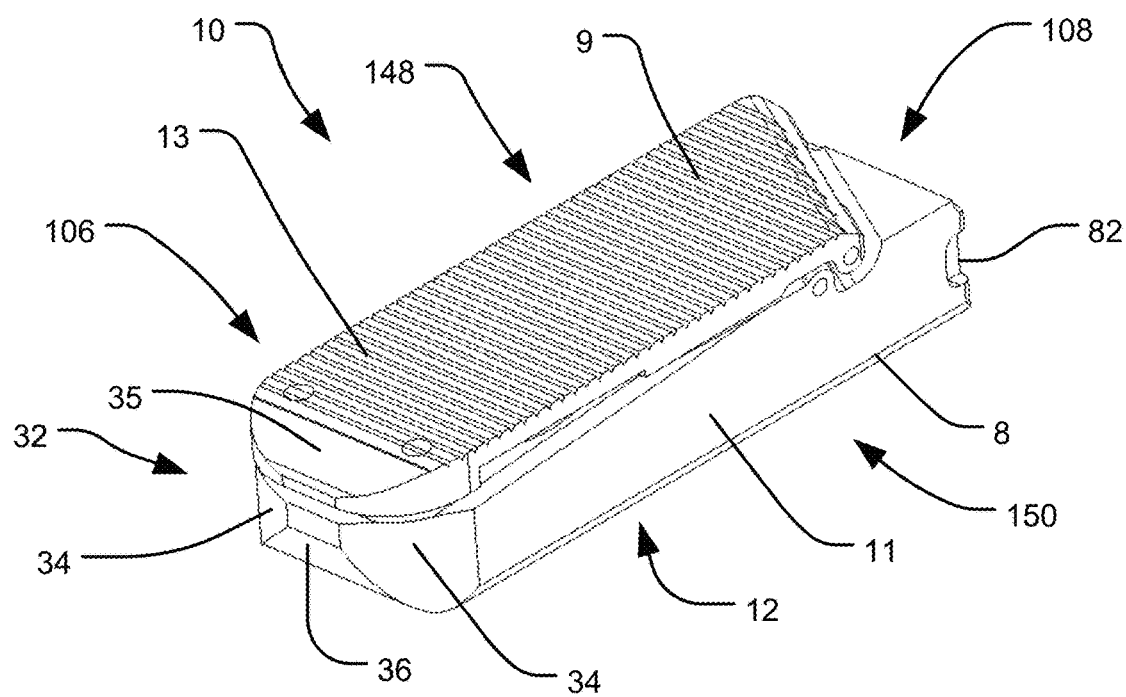
Figure 19A:
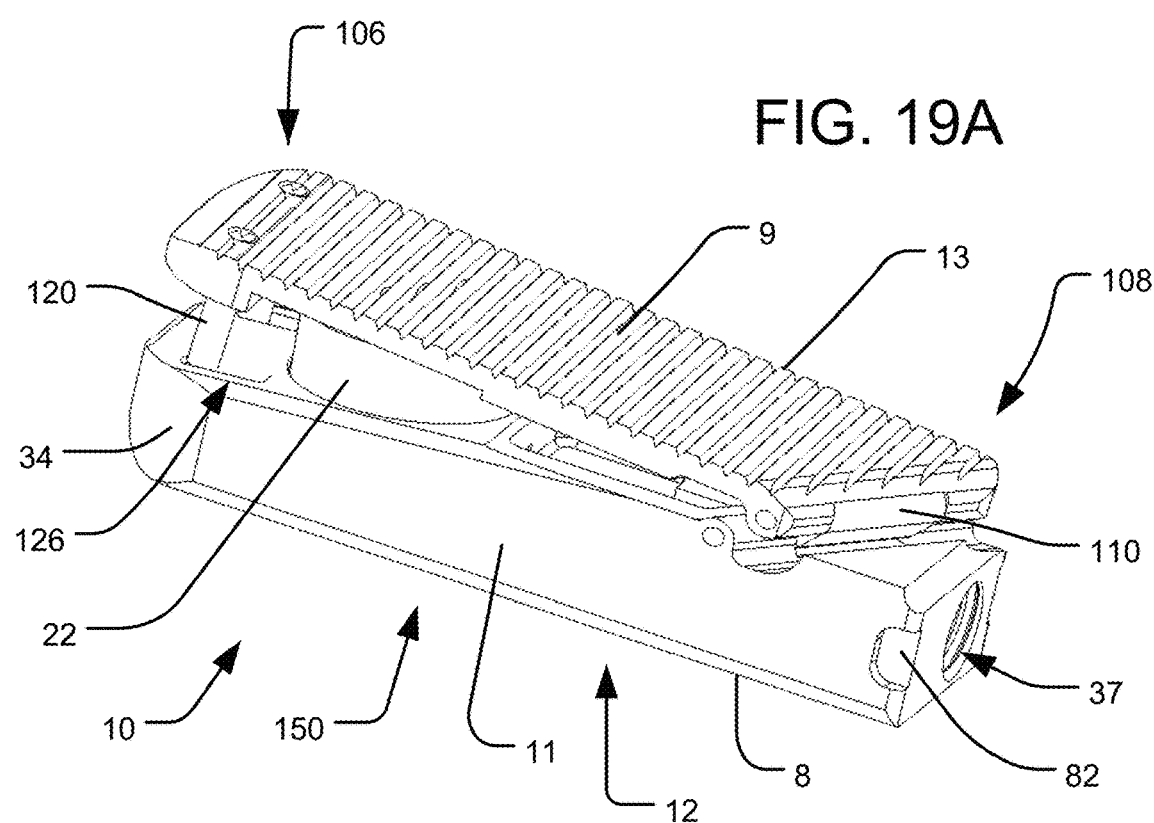
FIGS. 19A-B are perspective views of the embodiment of the implant of FIGS. 17A-B in an extended configuration.
Figure 19B:
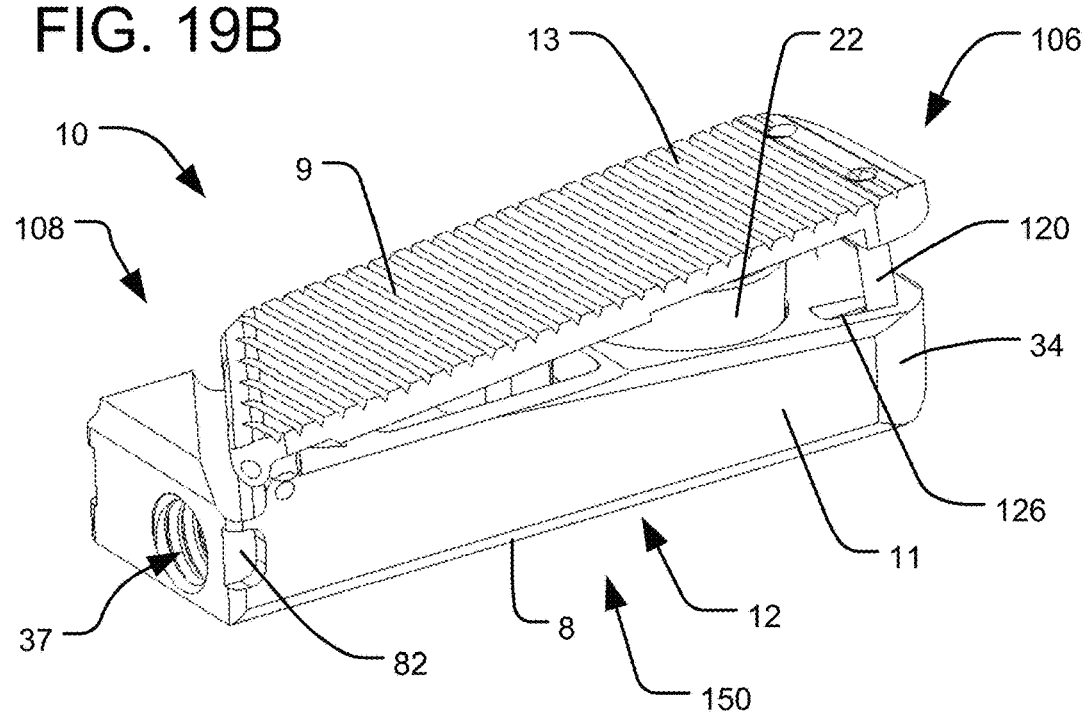
Figure 21A:
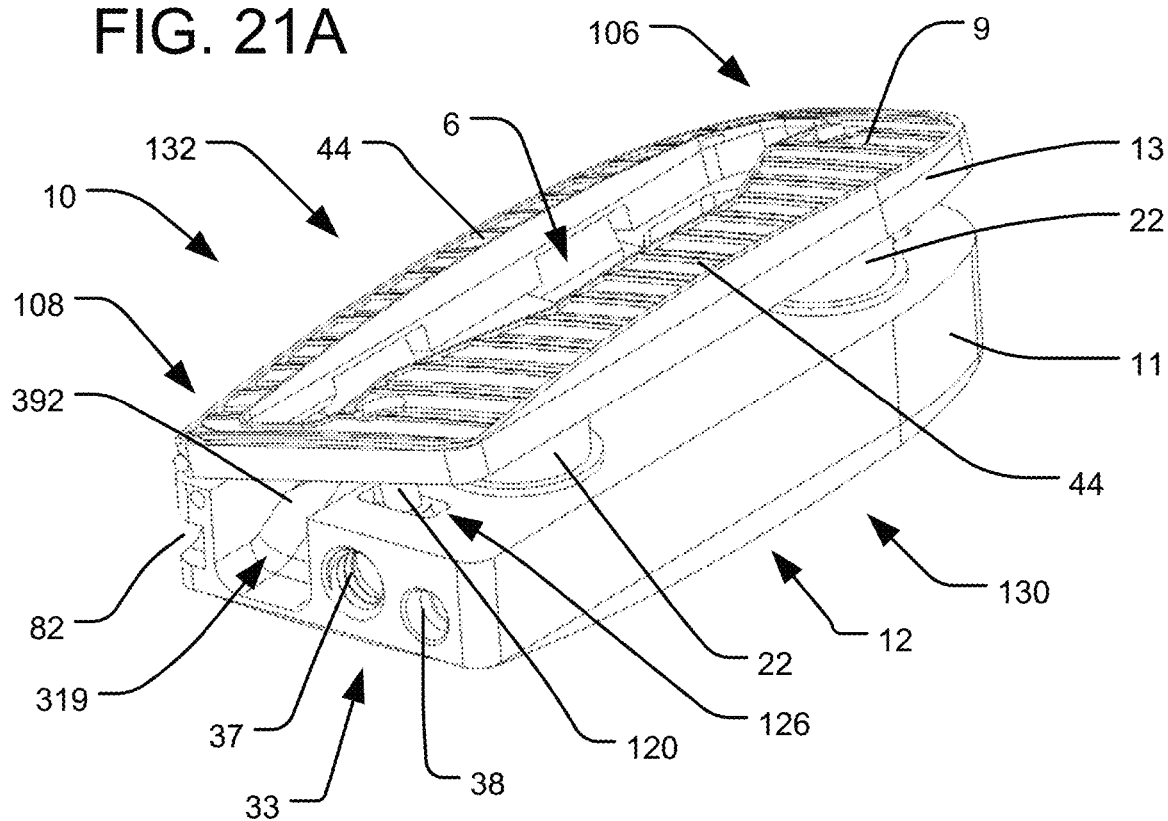
FIGS. 21A-B are top perspective views of an implant in accordance with another embodiment of the present invention in an extended configuration.
Figure 21B:
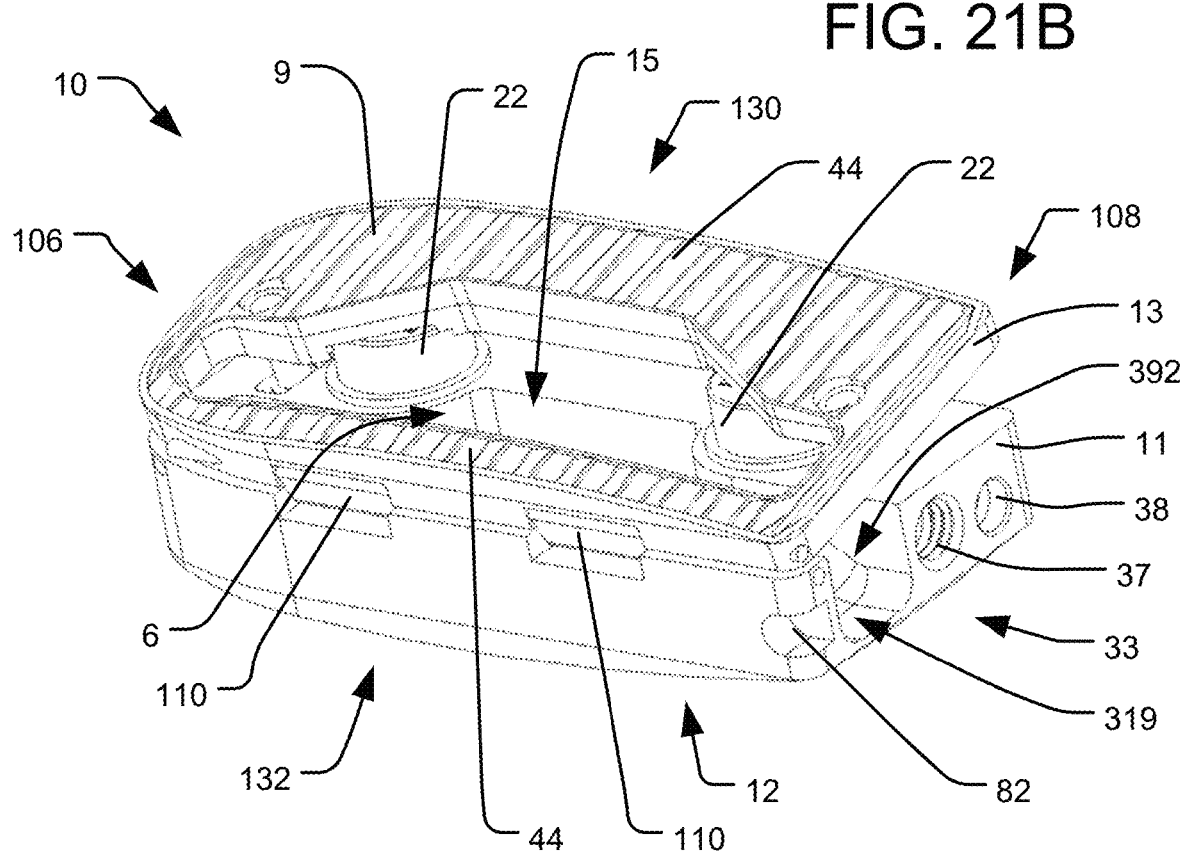
Figure 21C:
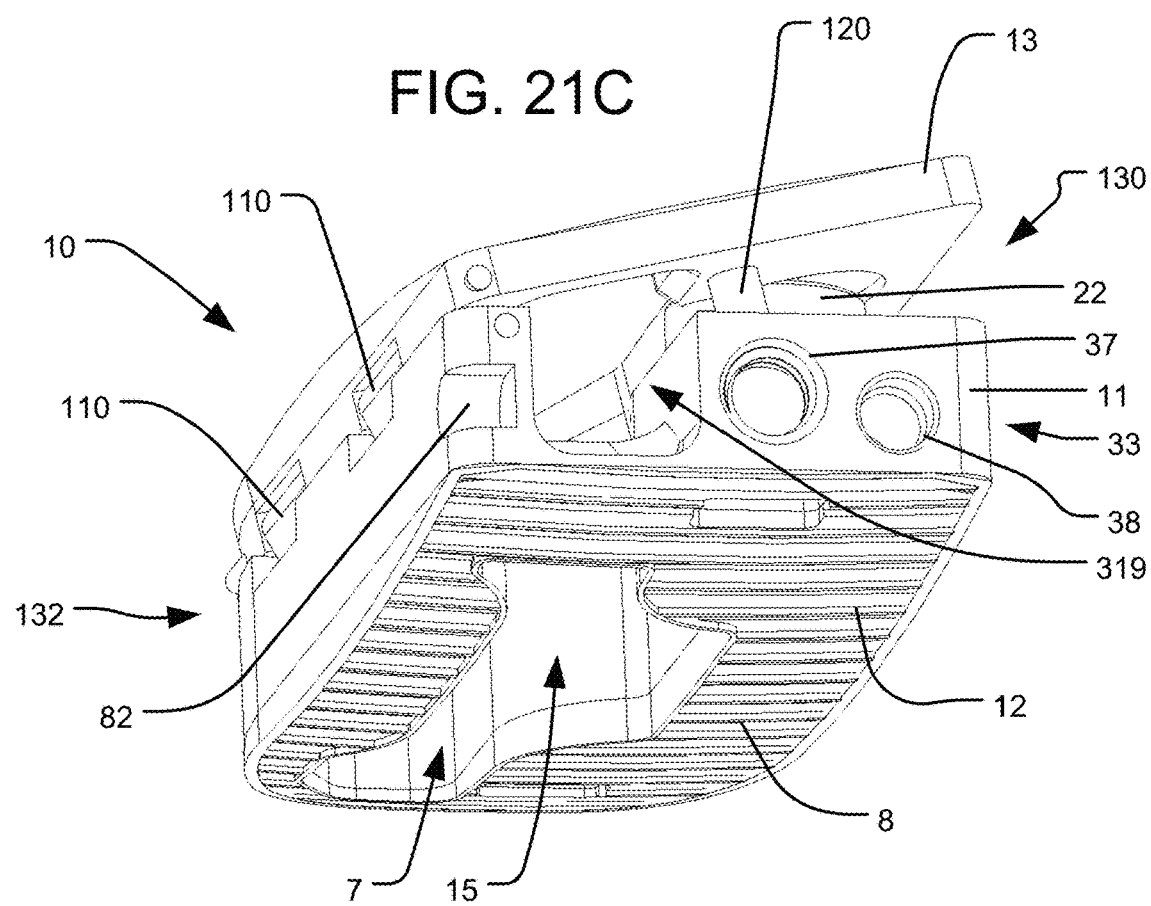
FIG. 21C is a bottom perspective view of the implant of FIGS. 21A-B.

In yet further embodiments of the present invention, which may be used in connection with PLIF, TLIF, or lateral implants, the connection between the top end plate 13 and the housing 11 that constrains the movement of the top end plate 13 during expansion and that defines the posterior expansion of the implant may be replaced with a four-bar linkage 142, as schematically illustrated in FIGS. 16A-B. That is, the top end plate 13 may be connected to the housing 11 by a posterior linkage 144 and an anterior linkage 146, both pivotably connected to the top end plate 13 and the housing 11 at each end. Moreover, the lengths of the linkages B and D, as well as the distances A, C between the connections, can be designed so as to produce the desired movement of the top end plate 13, which includes the desired expansion of the posterior end 132 (i.e., expanded height E' minus unexpanded height E at the posterior end 132). In order to prevent over-constraining the system of such an embodiment, the connection between the extension member (not shown) and the top end plate 13 may be designed to permit sliding between those components. For example, mating concave and convex surfaces as discussed above in connection with FIG. 14A may be employed.

Another embodiment of an implant 10 in accordance with the present invention is illustrated in FIGS. 17A-20B. The same reference numerals used above in connection with the components of the PLIF and lateral implants are used to indicate similar components in the implant of FIGS. 17A-20B. For example, the embodiment of FIGS. 17A-20B includes a top end plate 13 and a housing 11 defining one or more interior cavities 15 within it. Although the implant 10 illustrated in FIGS. 17A-20B does not include an opening 6 within the top end plate 13 like the other embodiments discussed above, this embodiment could include such an opening 6. The bottom 12 of the housing 11 may also include one or more openings (not shown) within it, which openings also communicate with the interior cavities 15. The bottom 12 of the housing 11 has a bottom end surface 8, and the top end plate 13 has a top end surface 9. The top end plate 13 is movably connected to the housing 11 on the opposite side of the housing 11 from the bottom end surface 8. The implant 10 is expandable by moving the top end plate 13 away from the housing 11, from the contracted configuration illustrated in FIGS. 17A-B to the extended configuration illustrated in FIGS. 19A-20B.

The implant 10 of FIGS. 17A-20B includes at least one extendable support element, which may be in the form of a piston 22 slidably received within a corresponding cylinder 16 defined within the housing 11. The piston may be driven by a pressurized fluid delivered through a channel as discussed above and in the '854 Application. The implant 10 may also include a locking system having inter-engaging locking elements, which locking elements may also be unlockable to allow the top end plate 13 to move back towards the housing 11, as discussed above. For example, the implant 10 may include a lower lock support 20 positioned within the housing 11 and a corresponding upper lock support (not shown) connected to the underside of the top end plate 13 as discussed above, as well as in the '620 Patent and the '854 Application. Like the other embodiments discussed above, the maximum expansion of the implant may be constrained by a stop member, such as one or more posts 120 slidably received through corresponding slots 126 in the housing 11, and the piston 22 may be angled so as to permit an unlocking mechanism to pass between the bottom of the cylinder 16 and the bottom end surface 8 of the housing 11, so as to engage the lower lock support 20 of the locking system, as discussed above The implant 10 of FIGS. 17A-20B preferably defines a leading nose 32 at a distal end 106 of the implant and an engagement region 33 at the proximal end 108 of the implant. The leading nose 32 may having a top tapered and/or rounded face 35 and a bottom tapered and/or rounded face 36. The leading nose 32 may additionally include inwardly directed side tapered and/or rounded faces 34. The engagement region 33 includes a delivery tool anchor 37 for secure attachment of the implant 10 to a delivery tool, as discussed above. The engagement region 33 may also include one or more engagement features, such as one or more recesses 82, which may be engageable by the delivery tool in order to act as an anti-rotation feature for securing the rotational orientation of the implant 10 with respect to the delivery tool anchor 37. The engagement region 33 may also contain one or more pressure input ports for delivery of a pressured fluid to the interior of the cylinder 16 in order to expand the implant. For example, the delivery tool anchor 37 may also serve as a pressure input port, as discussed above.

As with the above-discussed embodiments, the embodiment of FIGS. 17A-20B may also be configured to produce differential expansion at opposing ends of the implant. For example, like the embodiment of FIGS. 1-8B, the implant may be structured such that the top end plate 13 moves further away from the housing 11 at the distal end 106 of the implant than at the proximal end 108 of the implant. In addition, the top end plate 13 may move further away from the housing along one longitudinal side 148 of the implant than at the other longitudinal side 150 of the implant. Thus, the top end plate 13 may be configured to angulate within two orthogonal planes during expansion, or within one plane that is oriented at an oblique angle with respect to a longitudinal axis of the implant 10. As a result, the top end surface 9 of the top end plate 13 desirably forms a compound angle with respect to the housing 11 in the extended configuration, as shown in FIGS. 19C-20B. In order to accomplish such compound expansion, the connecting member (i.e., linkage 110) between the top end plate 13 and the housing 11 may be oriented along an oblique angle with respect to the longitudinal axis of the implant 10. The fulcrum 112 at the top of the piston 22 that is pivotably connected to the top end plate 13 may also be oriented at an oblique angle to the longitudinal axis (e.g., the fulcrum 112 may be oriented parallel to the linkage 110).

The embodiment of FIGS. 17A-20B may be particularly useful in an oblique transforaminal approach. In particular, such implant 10 may be inserted into an intervertebral space along a transforaminal approach, essentially similar to a TLIF technique, except that the implant may be positioned diagonally across the intervertebral space, rather than being positioned along the anterior portion of the intervertebral space. Thus, in order to produce the desired lordosis correction in that orientation, the top end plate 13 may be configured to angulate within multiple planes, as discussed above.

Another embodiment of an implant 10 in accordance with the present invention is illustrated in FIGS. 21A-26B. Such implant 10 is desirably structured to be used in a lateral approach. The same reference numerals used above in connection with the other, previously-described embodiments are used to indicate similar components in the implant of FIGS. 21A-26B. For example, the embodiment of FIGS. 21A-26B includes a top end plate 13 and a housing 11 defining an interior cavity 15 within it. The top end plate 13 may include an opening 6 within it, bounded by connecting members or struts 44 extending between the proximal and distal sides of the top end plate 13, which opening 6 communicates with the interior cavity 15. The bottom 12 of the housing 11 may also include an opening 7 within it, which opening also communicates with the interior cavity 15. Although only a single top opening 6, bottom opening 7, and interior cavity 15 are shown in the embodiment of FIGS. 21A-26B, multiple of each such structure may alternatively be provided, such as in the embodiment of FIGS. 9A-12B. The bottom 12 of the housing 11 of the embodiment of FIGS. 21A-26B has a bottom end surface 8, and the top end plate 13 has a top end surface 9. The top end plate 13 is movably connected to the housing 11 on the opposite side of the housing 11 from the bottom end surface 8. The implant 10 is expandable by moving the top end plate 13 away from the housing 11, from the contracted configuration illustrated in FIG. 25A to the extended configuration illustrated in FIGS. 21A-23, 25B, and 26B.

Figure 25A:
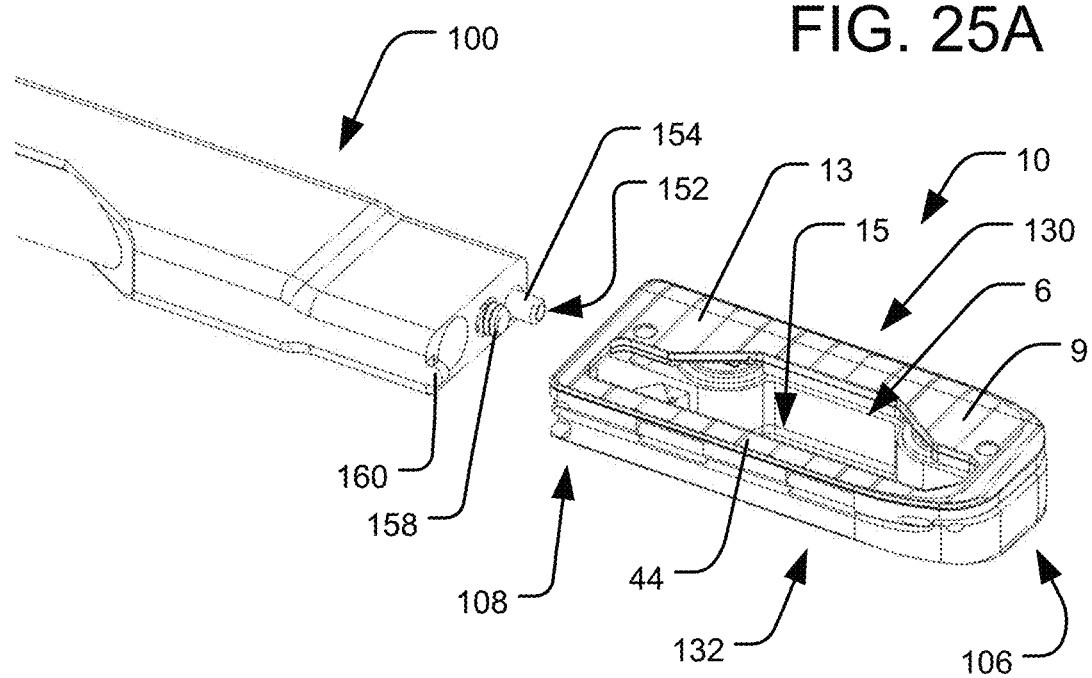
FIG. 25A is a perspective view of the embodiment of the implant of FIG. 21A-B in a contracted configuration, adjacent to the distal end of a delivery tool.
Figure 25B:
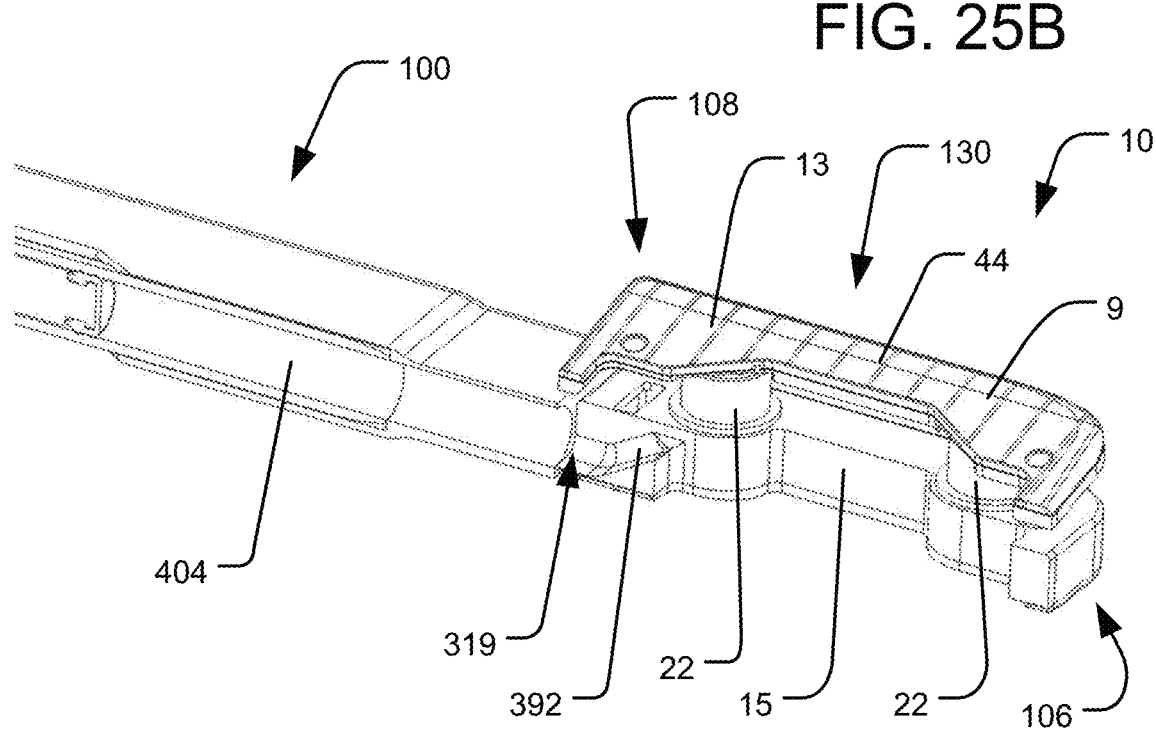
FIG. 25B is a perspective cross-sectional view of the embodiment of the implant of FIGS. 21A-B in a extended configuration, connected to the delivery tool.
Figure 26A:
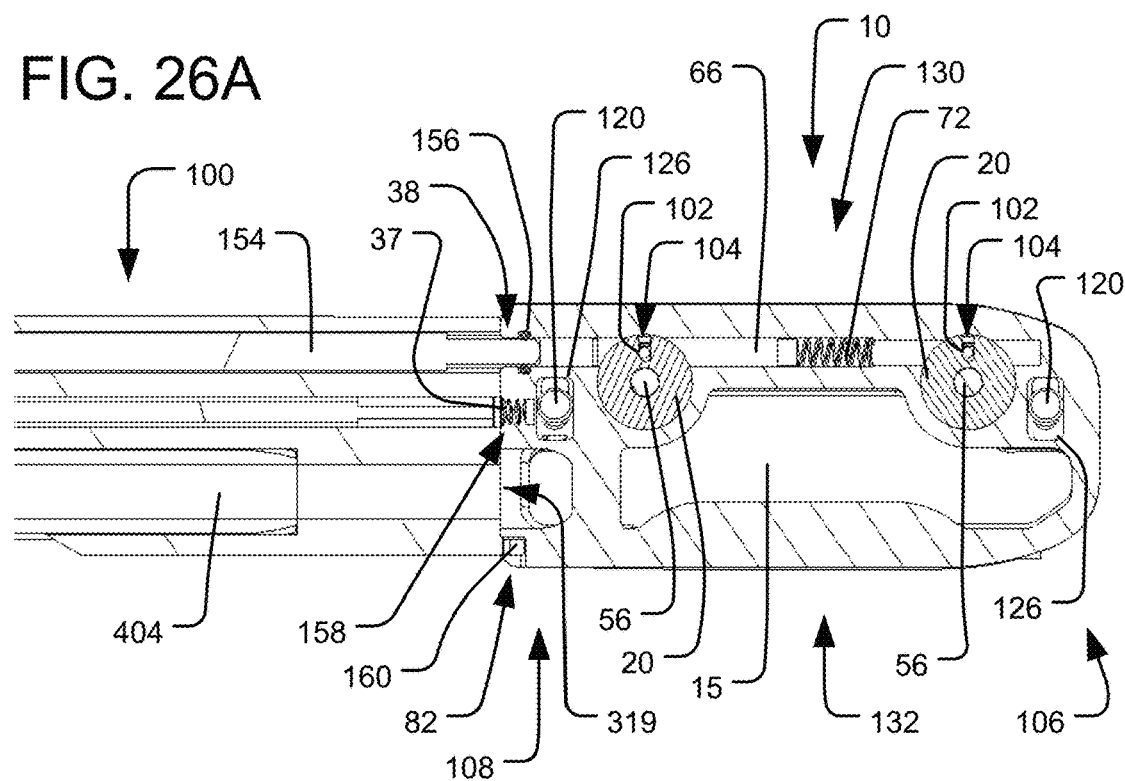
FIG. 26A is a cross-sectional top plan view of the embodiment of the implant of FIGS. 21A-B connected to the delivery tool.
Figure 26B:
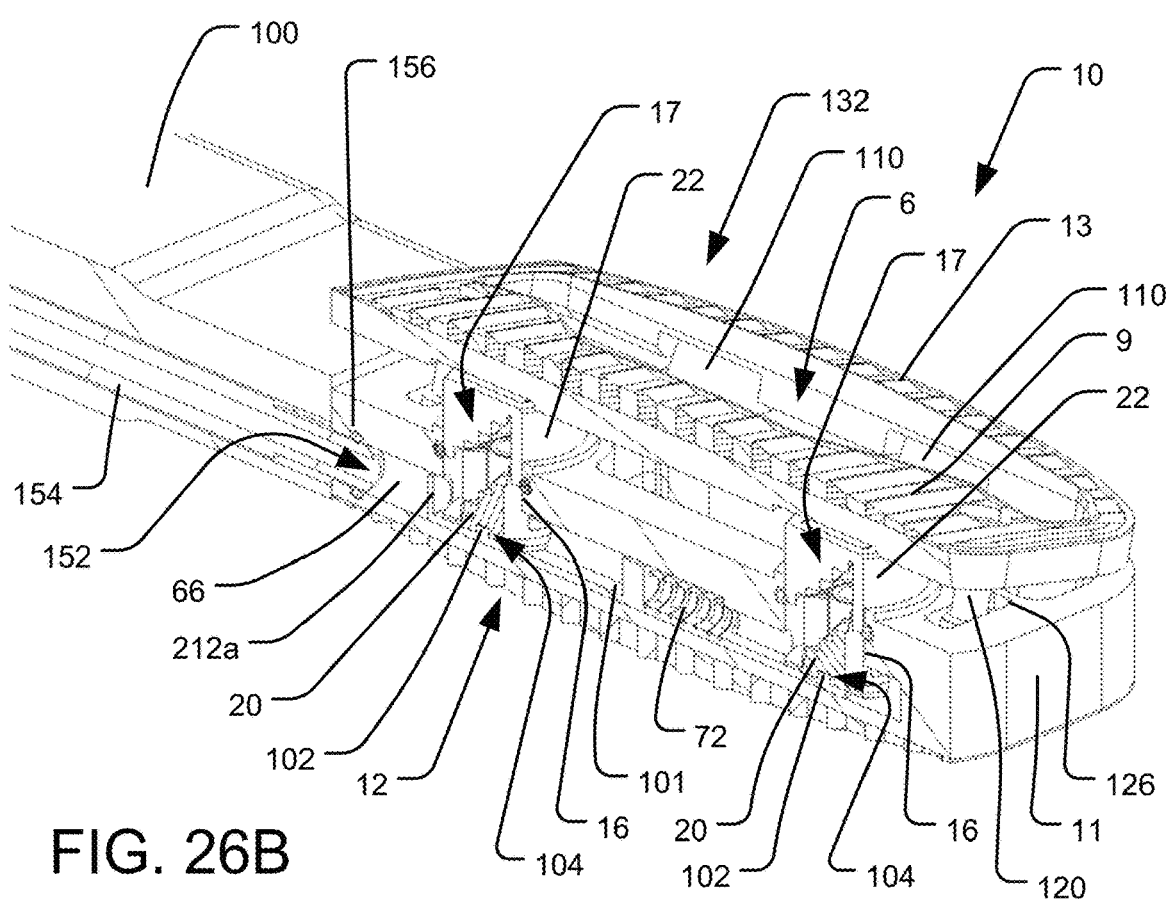
FIG. 26B is a perspective cross-sectional view of the embodiment of the implant of FIGS. 21A-B in an extended configuration, connected to the delivery tool.

Like the other lateral embodiments shown in FIGS. 9A-12B and 14A-15B and discussed above, the implant 10 of FIGS. 21A-26B may include two extendable support elements, although one or more than two may alternatively be provided. The extendable support elements are preferably in the form of pistons 22 slidably received within corresponding cylinders 16 defined within the housing 11. The pistons may be driven by a pressurized fluid delivered through a channel as discussed above and in the '854 Application. The implant 10 may also include a locking system having inter-engaging locking elements, which locking elements may also be unlockable to allow the top end plate 13 to move back towards the housing 11, as discussed above. For example, the implant 10 may include lower lock supports 20 positioned within the housing 11 and corresponding upper lock supports 17 (see FIG. 26B) connected to the underside of the top end plate 13, as discussed above, as well as in the '620 Patent and the '854 Application. As shown in FIG. 26B, the upper lock supports 17 may be positioned within and fixed with respect to the respective pistons 22. Indeed, the upper lock supports 17 may be integrally formed with the pistons 22. The structure and operation of the locking system of the embodiment of FIGS. 21A-26B is similar to those discussed above and in the '620 Patent and the '854 Application. For example, the lower lock supports 20 are rotatably received about corresponding axles 56 mounted within the cylinders 16, and bushings 58 may be provided at the top ends of the axles 56 to constrain the axial positions of the lower lock supports 20 with respect to the axles 56. Additionally, a pushable unlocking tether 212a may be engaged with the lower lock supports 20 so as to rotate the lower lock supports 20 in the unlock direction when the unlocking tether 212a is pushed in the distal direction. For example, the unlocking tether 212a may have an elongated extension 101 having laterally projecting tabs 102 coupled with corresponding receptacles 104 of the lower lock supports 20 so as to simultaneously rotate the lower lock supports 20 about the associated axles 56. The unlocking tether 212a may also be biased in the proximal direction by a linear spring 72. In addition, the pistons 22 may be angled so as to permit the unlocking tether 212a or other unlocking mechanism to pass between the bottom of the cylinders 16 and the bottom end surface 8 of the housing 11, so as to engage the lower lock supports 20 of the locking system. The maximum expansion of the implant may also be constrained by a stop member, such as one or more posts 120 slidably received through corresponding slots 126 in the housing 11.

As disclosed in the '854 Application, the housing 11 may include a channel 66 formed within it, which may serve as a pressure channel for delivering a pressurized fluid (e.g., saline) to the interior of the cylinders 16 in order to drive the movement of the pistons 22 to expand the implant. As shown in FIGS. 25A and 26A-B, the delivery tool 100 may include an outlet 152 for delivering the pressurized fluid. The outlet is desirably at the distal end of a fluid delivery cannula 154, which may project from the distal end of the delivery tool 100. The fluid delivery cannula 154 may be a separate structure positionable within or attached to the delivery tool 100, or the fluid delivery cannula 154 may be an integral part of the tool 100. As shown in FIG. 26B, the projecting distal end of the delivery cannula 154 desirably forms a sealing connection within the channel 66 due to its engagement with an o-ring 156 positioned within the channel 66. As shown in FIG. 26B, the unlocking tether 212a may be positioned within the pressure channel 66, although other embodiments (not shown) may have the unlocking tether 212a positioned in a distinct channel within the housing 11 from the pressure channel 66 that delivers the hydraulic fluid.

The implant 10 of FIGS. 21A-26B preferably shares many other similarities to the other embodiments discussed above. For example, the engagement region 33 at the proximal end of the implant 10 desirably includes a delivery tool anchor 37 for secure attachment to the delivery tool 100, such as via a threaded connection to a rotatable threaded member 158 of the delivery tool 100. The engagement region 33 may also include one or more engagement features, such as one or more recesses 82, which may be engageable by a finger 160 of the delivery tool 100 in order to act as an anti-rotation feature for securing the rotational orientation of the implant 10 with respect to the delivery tool anchor 37. As discussed above, the engagement region 33 may also contain one or more pressure input ports 38 for delivery of a pressurized fluid to the interior of the cylinders 16 in order to expand the implant. Although the delivery tool anchor 37 may serve as the pressure input port, as discussed in connection with other embodiments above, the pressure input port 38 in the embodiment of FIGS. 21A-26B may be a different opening in the engagement region 33, as shown in FIGS. 21A-24.

Figure 23:
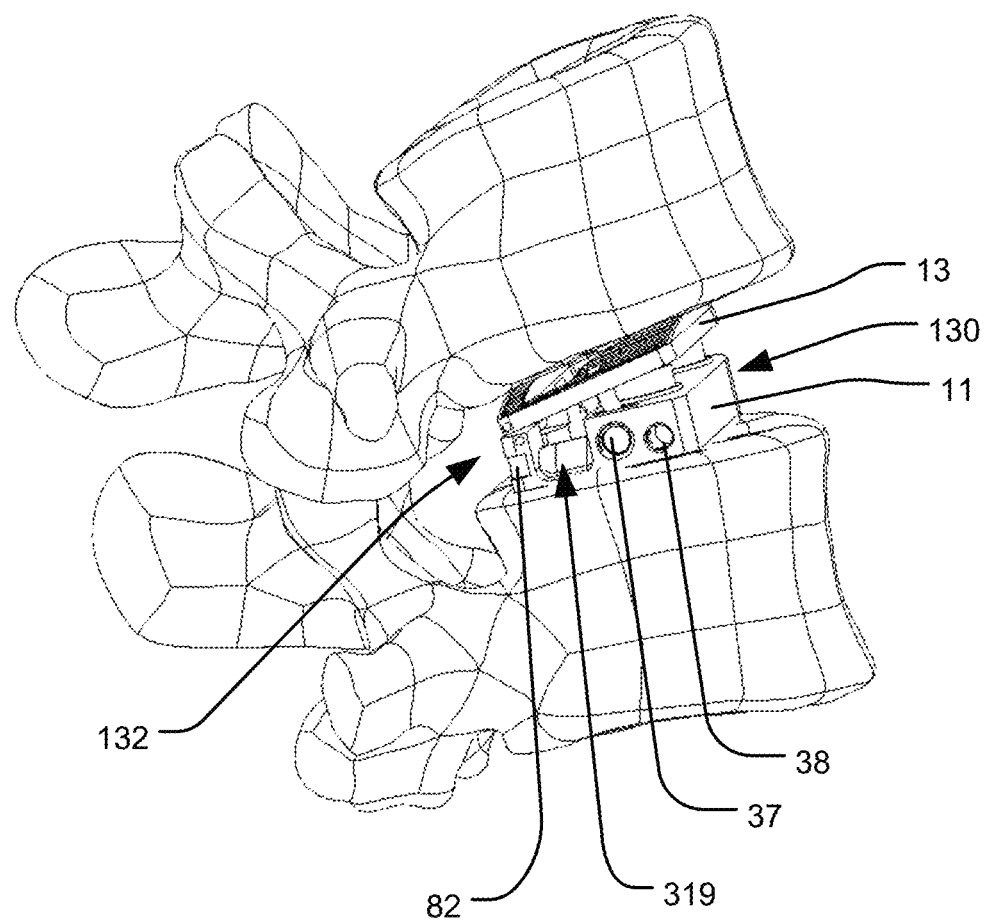
FIG. 23 is a rear perspective view of the implant of FIGS. 21A-B in an extended configuration between two vertebral bodies.
Figure 24:
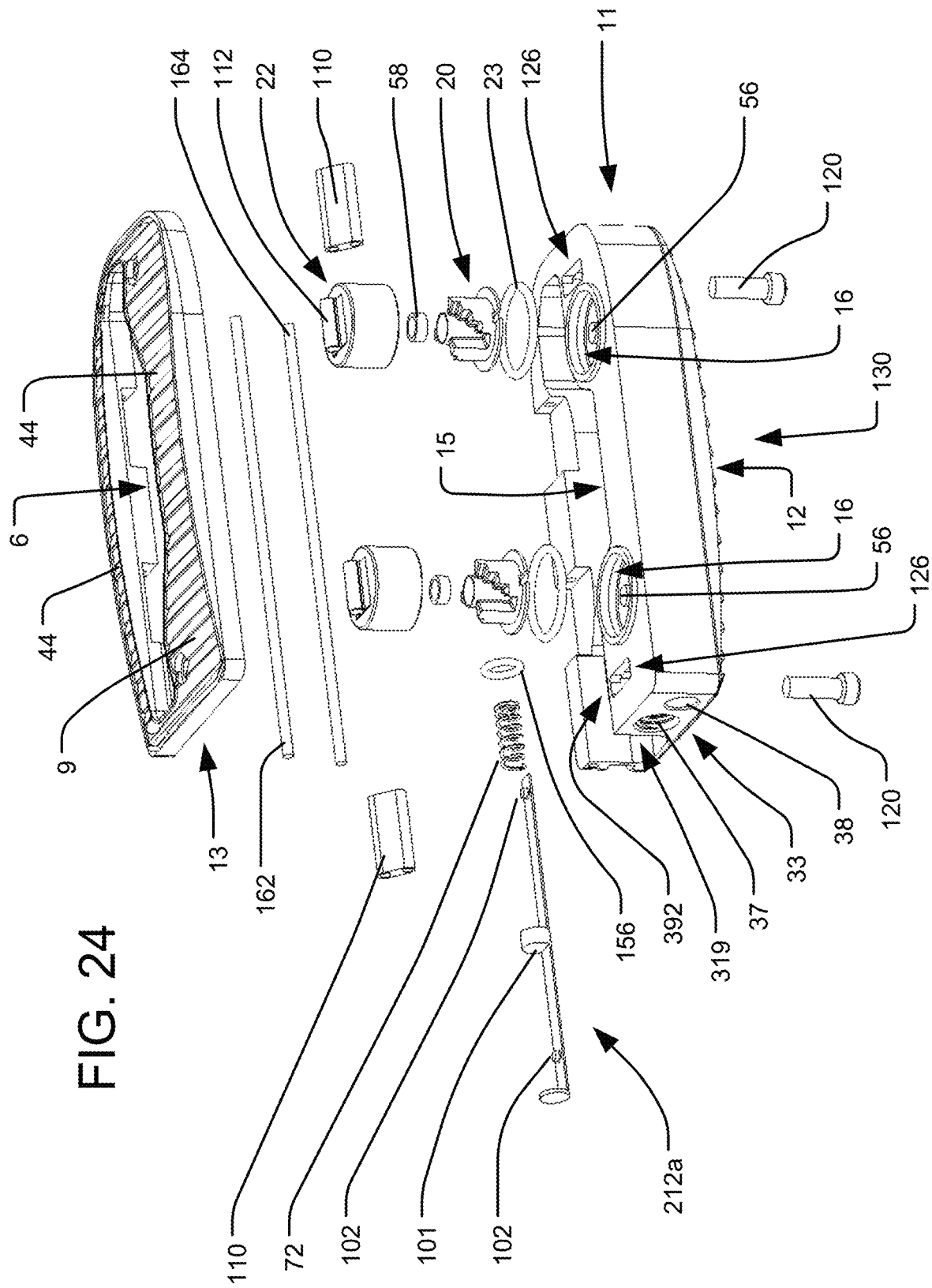
FIG. 24 is an exploded, perspective view of the embodiment of the implant of FIGS. 21A-B.

Similar to the embodiments disclosed in '550 Patent, the implant 10 may also include a bone graft input/infusion port 319 structured to receive autologous and/or allogeneic bone graft, a bone growth enabling matrix, and/or bone growth stimulating substances after the implant is inserted into the body. The port 319, which is desirably located at the proximal end of the implant, such as part of the engagement region 33, communicates with the interior cavity 15 via passage 392. For example, the graft material may be supplied to the implant by a bone graft supply line 404 of the insertion tool 100, which supply line 404 may define a channel that communicates with the passage 392 in the implant 10 when the insertion tool 100 is connected to the implant 10, as shown in FIG. 25B. Thus, after the implant 10 is inserted between two vertebrae (as shown in FIG. 23), and either before or after expansion of the implant 10, but while the insertion tool 100 is still connected to the implant 10, graft material may be supplied to the interior cavity 15 of the implant via the bone graft supply line 404 of the insertion tool 100. Such supply may cause the graft material to flow out of the openings 6, 7 in the top and bottom of the implant, as well as possibly through the opened space between the top end plate 13 and the housing 11, such that the graft material may flow into and at least partially fill the disc space, where it can desirably promote fusion of the adjacent vertebrae.

In other embodiments, graft material may be supplied through the port 319 and passage 392 and into the interior cavity 15 of the implant 10 from any one of the embodiments of graft injector assemblies disclosed in U.S. Patent Application Publication No. 2015/0112352, the disclosure of which is incorporated by reference herein as if fully set forth herein, and such graft injector assemblies may be loaded using the devices and methods disclosed in U.S. patent application Ser. No. 15/241,339 filed Aug. 19, 2016, entitled Bone Graft Delivery Loading Assembly, the disclosure of which is also incorporated by reference herein as if fully set forth herein. Furthermore, any of the other embodiments of the implants 10 disclosed herein and discussed above may also include a bone graft input/infusion port 319 and associated passage 392 for likewise supplying bone graft material to the interior cavity 15 of the implant.

As with the above-discussed embodiments, the embodiment of FIGS. 21A-26B may also be configured to produce differential expansion at opposing ends of the implant. Since the lateral embodiment of FIGS. 21A-26B is desirably inserted laterally into the disc space between two vertebral bodies, the differential expansion may be between the opposing ends of the implant on either side of the longitudinal axis, rather than between the proximal 108 and distal 106 ends of the implant. In that regard, the lateral implant is desirably positioned in the spine such that one of those ends is an anterior end 130 of the implant and the other end is a posterior end of the implant 132. Thus, the embodiment of FIGS. 9A-12B may allow for lordosis correction by providing expansion at both the anterior and posterior ends of the implant, with the anterior end 130 expanding by a greater amount than the posterior end 132. To accommodate that differential expansion, and the resulting rotation of the top end plate 13, the pistons 22 may be pivotably connected to the top end plate 13 by respective fulcrums 112. Similarly, the top end plate 13 may be connected to the housing 11 at the posterior end 132 of the implant by one or more connecting members, such as by rotatable linkages 110 pivotably connected to the top end plate 13 and the housing 11. As shown in FIGS. 21B, 22A, and 23, multiple (e.g., two) linkages 110 may be provided along the posterior end 132 of the implant, rather than a single linkage as in the other embodiments described above. Providing more linkages 110 in that manner may desirably divide the applied shear force over the various linkages, thus reducing the shear force experienced by any one linkage. Such linkages 110 may be pivotably connected to the top end plate 13 by a common upper pin 162, and the linkages may be pivotably connected to the housing 11 by a common lower pin 164. In an alternative embodiment (not shown), however, separate pins may be provided for each linkage 110 connection, rather than common pins as shown.

Figure 22:
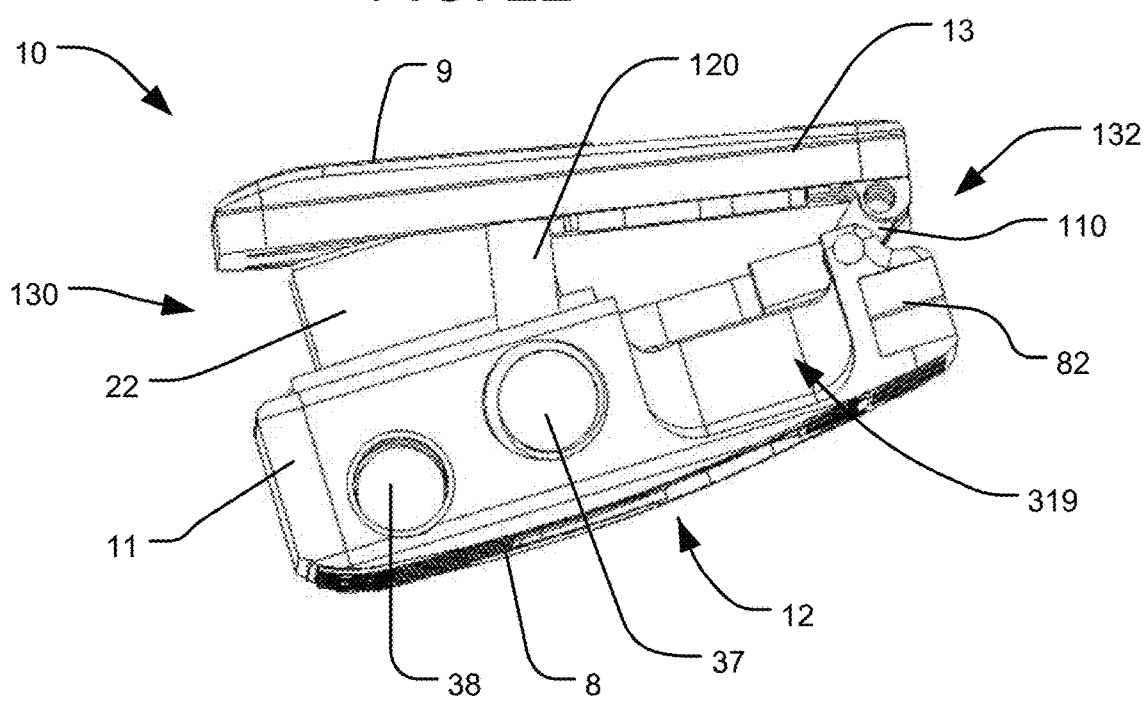
FIG. 22 is a rear elevation view of an embodiment similar to that of FIGS. 21A-B in an extended configuration.

Any of the embodiments of the implant 10 disclosed above may be reversed so that they may be inserted along a different approach. For example, FIG. 22 depicts a version of the implant 10 of FIGS. 21A-21C mirrored about its midline. Such mirrored implant 10 may be inserted along a lateral approach to the spine from the opposite side of the body to that on which the implant of FIGS. 21A-C may be inserted.

Although the embodiments of the implant 10 disclosed above included pistons 22 and cylinders 16 driven by hydraulic pressure to expand the implant 10, other forms of extendable support elements may alternatively be used. For example, as disclosed in the '620 Patent, the implant 10 may be expanded by bellows, rotating cam lift mechanisms, rotating screw lift mechanisms, or other such devices.

The embodiments of the implant 10 discussed above involve expansion wherein the entire top end plate 13 moves away from the housing 11, by providing some expansion at the posterior end of the implant, although less expansion than at the anterior end of the implant. In other variations (not shown) of any of the above-discussed embodiments, however, there may be no expansion provided at the posterior end of the implant. For example, the connecting member could be replaced by a pin connection at the posterior end of the implant, which pin connection permits rotation of the top end plate 13 about the pin connection but does not involve the top end plate 13 moving away from the housing 11 at the posterior end.

In other embodiments in accordance with the present invention, the implant 10 may instead be constructed to provide greater expansion at a different end of the implant (e.g., at the posterior end), by employing substantially the same mechanisms discussed above, except in rearranged locations within the implant. For example, the locations of the components controlling the expansion, such as the extendable support elements and linkages, may be mirrored within the implant. That way, the implant 10 can be used to provide curvature correction in a different direction than that discussed above. Additionally, or alternatively, the surgeon can modify the direction and/or plane of the applied curvature correction by varying the orientation of the implant with respect to the spine. For example, any one of the implants can be inserted into and/or reoriented within the disc space such that the implant is oriented with respect to the longitudinal axis of the spine so as to provide curvature correction in a desired longitudinal plane and in a desired direction within that plane.

Some or all of the components or portions of components of the implants 10 disclosed herein may be created by an additive manufacturing or 3D printing process, e.g., using Laser Rapid Manufacturing (LRM) technology. Additionally, or alternatively, some of the components or portions of components may be manufactured from a porous material, such as a porous metal. Such porous metal may be in the form of a porous, commercially-pure titanium matrix or a porous, titanium alloy (e.g., a Ti6A14V alloy), such as those manufactured by Howmedica Osteonics Corp. under the trademark TRITANIUM®. Examples of additive manufacturing processes for creating some or all of the components of the implants 10 disclosed herein, including some such processes for creating porous materials, are disclosed in U.S. Pat. Nos. 7,537,664; 8,147,861; 8,350,186; 8,728,387; 8,992,703; 9,135,374; and 9,180,010, as well as U.S. Patent Application Publication No. 2006/0147332, all of which are hereby incorporated by reference herein as if fully set forth herein. In one example, the top end plate 13 and the bottom 12 of the housing 11 may include a porous titanium matrix formed via 3D printing, and then various features of the implant 10 may be further defined by machining of those components. For example, surface features to increase frictional engagement with the vertebrae above and below the implant may be defined in the porous matrix by machining the bottom end surface 8 and the top end surface 9. The porous material may also be supplemented by or replaced with solid or denser material in at least portions of the implant 10, however. For example, the tops of projecting ridges and other features along the top and bottom end surfaces 9, 8 may be formed from solid material, while the surrounding base portions that interconnect those features are formed from a porous matrix. Solid (non-porous) material may also be used in the portions of the implants 10 that enclose the hydraulic fluid. Solid material, which may be constructed with a smooth surface finish, may also be used along the interfaces between components that slide with respect to one another. Solid material may also be used in portions of the implants 10 where additional structural integrity is needed due to the loads that will be applied by the spine. For example, the periphery of the top end plate 13 may be constructed of solid material. In another example, the struts 44 may be constructed of solid material, in order to increase the strength to the top end plate 13. In an alternative, portions of the implants 10 where additional structural integrity is needed may be constructed of a porous metal material, but the density of that material may be increased in those portions. Examples of implants having both solid and porous portions, as well as methods of creating the same, are disclosed in U.S. Provisional Patent Application No. 62/245,004, filed on Oct. 22, 2015, and U.S. Patent Application Publication No. 2016/0199193, the entire disclosures of which are hereby incorporated by reference herein as if fully set forth herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of performing interbody fusion, the method comprising:
   positioning a spinal implant between a first vertebral body and a second vertebral body, wherein the spinal implant includes a top plate including a first surface to engage the first vertebral body, a housing including a second surface to engage the second vertebral body, and a hydraulic system between the top plate and the housing; and
   inducing, based on an actuation force to the hydraulic system, movement of the top plate away from the housing at both a first end portion and a second end portion of the spinal implant, wherein
   the induced movement of the top plate away from the housing is guided by a linkage, such that the top plate moves away from the housing by a first distance at the first end portion of the implant and a second distance at the second end portion of the implant, and the first distance is greater than the second distance.

2. The method of claim 1, wherein the linkage is positioned at the second end portion of the implant such that the induced movement guides the top plate away from the housing by constraining movement of the top plate at the second end portion of the implant.

3. The method of claim 1, wherein the hydraulic system is located at the first end portion of the spinal implant.

4. The method of claim 1, wherein the actuation force includes delivering a pressurized fluid to the hydraulic system.

5. The method of claim 1, further comprising inducing, based on the actuation force, movement of the linkage.

6. The method of claim 1, wherein the linkage is a rotatable linkage including a first end and a second end, the first end of the linkage being pivotably connected to the top plate and the second end of the linkage being pivotably connected to the housing.

7. The method of claim 6, wherein the induced movement of the top plate away from the housing is guided by the rotatable linkage.

8. The method of claim 1, wherein the induced movement is constrained by a stop member extending between the top plate and the housing.

9. The method of claim 1, further comprising locking a position of the top plate with respect to the housing.

10. The method of claim 9, wherein the locking is provided by a locking system that includes a lower lock support positioned within the housing and a corresponding upper lock support connected to an underside of the top plate.

11. The method of claim 10, wherein the upper lock is integrally formed with the hydraulic system.

12. The method of claim 9, further comprising unlocking the position of the top plate with respect to the housing.

13. The method of claim 1, wherein the induced movement is provided by sliding a piston away from a bottom of a cylinder in the housing.

14. The method of claim 1, wherein the induced movement is provided via a delivery tool.

15. The method of claim 1, wherein the hydraulic system is angled toward the first end portion of the implant.

* * * * *